United States Patent [19]

Guzman

[11] Patent Number: 5,045,172
[45] Date of Patent: Sep. 3, 1991

[54] CAPILLARY ELECTROPHORESIS APPARATUS

[75] Inventor: Norberto Guzman, East Brunswick, N.J.

[73] Assignee: Princeton Biochemicals, Inc., Princeton, N.J.

[21] Appl. No.: 270,788

[22] Filed: Nov. 14, 1988

Related U.S. Application Data

[63] Continuation-in-part of Ser. No. 125,544, Nov. 25, 1987, abandoned.

[51] Int. Cl.$^5$ .................. G01N 27/26; B01D 57/02
[52] U.S. Cl. .......................... 204/299 R; 204/180.1; 204/183.3
[58] Field of Search ............ 204/299 R, 180.1, 183.3; 73/864.23, 864.18, 863.01, 864.24, 864.25; 422/64

[56] References Cited

U.S. PATENT DOCUMENTS

| | | | |
|---|---|---|---|
| 3,793,180 | 2/1974 | Flower et al. | 204/183.3 X |
| 3,918,913 | 11/1975 | Stevenson et al. | 73/863.72 |
| 3,941,678 | 3/1976 | Akiyama | 204/244 R |
| 3,948,753 | 4/1976 | Arlinger | 204/183.3 X |

OTHER PUBLICATIONS

J. Jorgenson, "Capillary Zone Electrophoresis", *New Directions in Electrophoretic Methods*, J. Jorgenson Ed., ACS Symposium Series 335, American Chemical Society, Washington, D.C. (1987).

Rose, Jr. and Jorgenson, "Characterization and Automation of Sample Introduction Methods for Capillary Zone Electrophoresis", Analytical Chemistry, vol. 60, No. 7, Apr. 1, 1988, pp. 642-648.

*Primary Examiner*—John F. Niebling
*Assistant Examiner*—John S. Starsiak, Jr.
*Attorney, Agent, or Firm*—Robert A. Green

[57] ABSTRACT

The apparatus includes a capillary tube having input and output ends and having a detector coupled thereto. A rotatable table is provided at each end of the capillary tube and each table includes sample cups for containing samples to be analyzed, and, if desired, a medium to be introduced into the capillary for transporting a sample substance to be analyzed. An electrode is provided adjacent to each end of the capillary tube for applying electrical potential across the capillary tube to cause charged particles of a sample to flow through the capillary tube and past said detector which detects the components of the sample.

Electronic means, including a computer, are provided for causing various portions of the apparatus to operate automatically when performing an analytical operation.

40 Claims, 19 Drawing Sheets

CAPILLARY ELECTROPHORESIS APPARATUS

CROSS-REFERENCE TO RELATED APPLICATIONS

This application is a continuation-in-part of application Ser. No. 125,544 filed Nov. 25, 1987, now abandoned.

BACKGROUND OF THE INVENTION

Electrophoresis is a phenomenon in which charged particles move in a conductive buffer medium or fluid across which a potential difference is applied. The migration is toward an electrode carrying charge opposite to that of the particles.

Electrophoresis is one of the most important methods available for the investigation of biological materials, and probably the most efficient procedure for the separation and detection of proteins and other matter.

Electrophoresis separation relies on the differential speeds of the migration of differently charged particles in an electrical field. The migration speed is primary a function of the charge on the particle and the field strength applied and the charge on a particle is determined by the pH of the buffer medium. The most important application of this technique in biomedical research and clinical chemistry laboratories, is in the electrophoretic separation of proteins, nucleic acids, their component peptides and oligonucleotides, as well as complex macromolecules such as lipoproteins.

Several different systems are known for practicing electrophoretic separation. For example, one system, known as zonal procedures, has advantages but it also has certain limitations. Some of the most common limitations are: The amount of sample required in order to reveal the components by the common staining procedures is usually large, the preparation of the apparatus and complete system involved in the electrophoretic separation is commonly tedious and time consuming, the time required to obtain complete separation of the components is often hours, the time required to reveal the components and to obtain some quantitation of the separated substances is also commonly hours, the yield of recovery of the components as biological actives in most cases is very low, the reproducibility of the electrophoretic separation is not 100 percent accurate, and the automation to perform the entire system operation is almost lacking.

Capillary electrophoresis has been shown to be a technique for obtaining high separation efficiency. For some proteins and small peptides, separation efficiencies of approximately one million to about a few million have been demonstrated. In general, this technique utilizes a fused silica (quartz) capillary with an inside diameter ranging from about 25 microns to about 200 microns, and a length ranging from about 10 centimeters to about 100 centimeters. Since the entire volume of the column is only 0.5 to about 30 microliters (yielding probably the smallest total surface area of column chromatography), the injection volume is usually in the low nanoliters range. As a consequence, the sensitivity of this technique is quite high and it is possible to obtain quantitation in the order of picomoles (and probably femtomoles or attomoles) using fluorescence, electrochemical, laser induced fluorescence, and mass spectrometry detectors, and to obtain quantitation in the order of nanomoles using ultraviolet detectors.

In capillary electrophoresis, the efficient heat transfer from small diameter capillaries permits application of unusually high voltages ranging from about 5,000 volts to about 30,000 volts while maintaining a low current, in the range of about 10 microamperes to about 90 microamperes. The application of high voltages promotes more effective separations and increases the speed of analysis to record times of about 5 to 40 minutes.

In addition to high separation efficiency (theoretical plates), fairly high resolution, high sensitivity quantitation, and small migration (retention) times, capillary electrophoresis presents a few more advantages over conventional electrophoresis, and in general, other chromatographic procedures. Some of these advantages are: a) application to a wide variety of samples ranging from small ions to proteins or other macromolecules of molecular weights of approximately 290,000 daltons or higher (such as DNA fragments, viruses, and subcellular particles) by using essentially the same column and probably the same conditions of electrophoretic separation; b) capillaries should provide an ideal system to explore nonaqueous media, particularly with substances which are highly hydrophobic; c) capillaries are reusable many times making the electrophoretic separation system very practical and economical; d) on-line electronic detection permits good quantitation and further enhances possibilities for fully automatic operation making the capillary electrophoresis system of higher resolution, greater speed, and better accuracy than conventional methods.

In the prior art, it is generally known that a material, containing mixtures of substances to be analyzed, can be passed along a capillary tube and through a detector under the influence of an applied voltage. The applied voltage charges the substances and the charges on the substances determine their spacing and their speed of passage along the capillary tube.

The prior art, U.S. Pat. Nos. 3,620,958, 3,948,753 and 4,459,198, show electrophoresis apparatus including a capillary tube connected between two containers for containing the substance to be analyzed and having electrical potential applied between the two containers and across the capillary tube. While the various forms of apparatus shown in these patents are apparently useful, they require large concentrations of samples to be analyzed and none is capable of being automated or provides teaching related to automation.

The present invention provides high voltage capillary electrophoresis apparatus including, among other things, means for feeding small concentrations of sample material into a capillary tube, automatically applying the proper voltage to cause the components of the sample to be charged and to flow along the capillary tube through a detector wherein the components are detected and a printed record is made. The apparatus can then automatically repeat the process for the analysis of multiple samples.

The basic apparatus of the invention is susceptible of many modifications in its various parts including the capillary tube portion. In addition, the method of detection of samples may be varied and the collection of samples can be modified. The invention can also be adapted to measure electroosmotic flow in a capillary.

DESCRIPTION OF THE INVENTION

Figure 1:
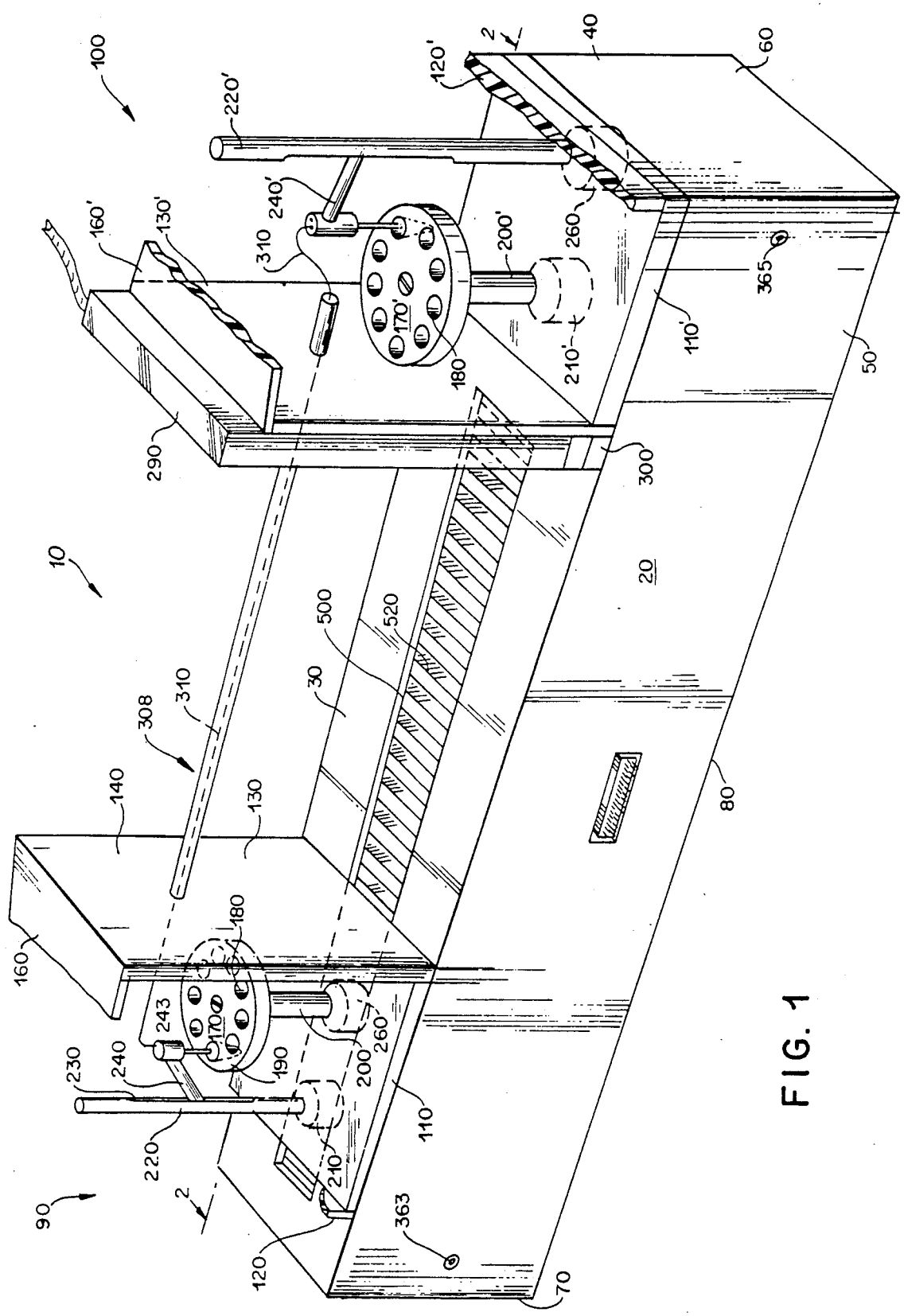
FIG. 1 is a perspective view of the rear of apparatus embodying the invention.

The automated electrophoresis apparatus of the invention 10, shown from the rear in FIG. 1, includes a base support member to which various pieces of operating equipment are secured. The support member 20 is box-like and includes a top wall 30, a front wall 40, a rear wall 50 and end walls 60 and 70 all of which extend downwardly from the top wall. A bottom cover plate 80 (FIGS. 1 and 2) is secured to the support member 20 and provides a flat support surface for the apparatus 10.

The support member 20 is of metal or a plastic and carries on top wall 30 a left hand box 90 and a right hand box 100 as seen in FIG. 1. The left hand box 90 includes an insulating base plate 110, of a metal or plastic, secured to top wall 30 and a transparent enclosure, of plexiglass or the like, including (FIGS. 1 and 2) left and right side walls 120 and 130, front and rear walls 140 and 150 and a top wall 160. The top wall 160 is a cover for the box 90 and is adapted to be lifted off the box by means of knob 162 to provide access to the interior thereof. The enclosure for box 90 is suitably secured to the base 110.

Box 90 is provided with a rotatable horizontal table 170 having a circular array of holes or apertures 180 in which fluid sample cups 190 are seated. The table is detachably secured to the upper end of a vertical post 200 so that tables with different numbers of holes or different sizes of holes or with other features can be secured to the post. The post 200 extends through and beneath the top wall 30 of the support member 20 (FIGS. 2 and 3) where it is suitable connected to a small motor 210 which is used to rotate the post 200 and table 170. The motor 210 is secured to the lower surface 32 of the top wall 30 and is of a type which permits the post 200 or an extension thereof to extend through it to be driven thereby.

The lower end of the post 200 carries a horizontal disk 203 (FIG. 3) which rotates with the post and includes a slot 205 which is adapted to operate with an optical sensor 212 positioned adjacent thereto.

Figure 2:
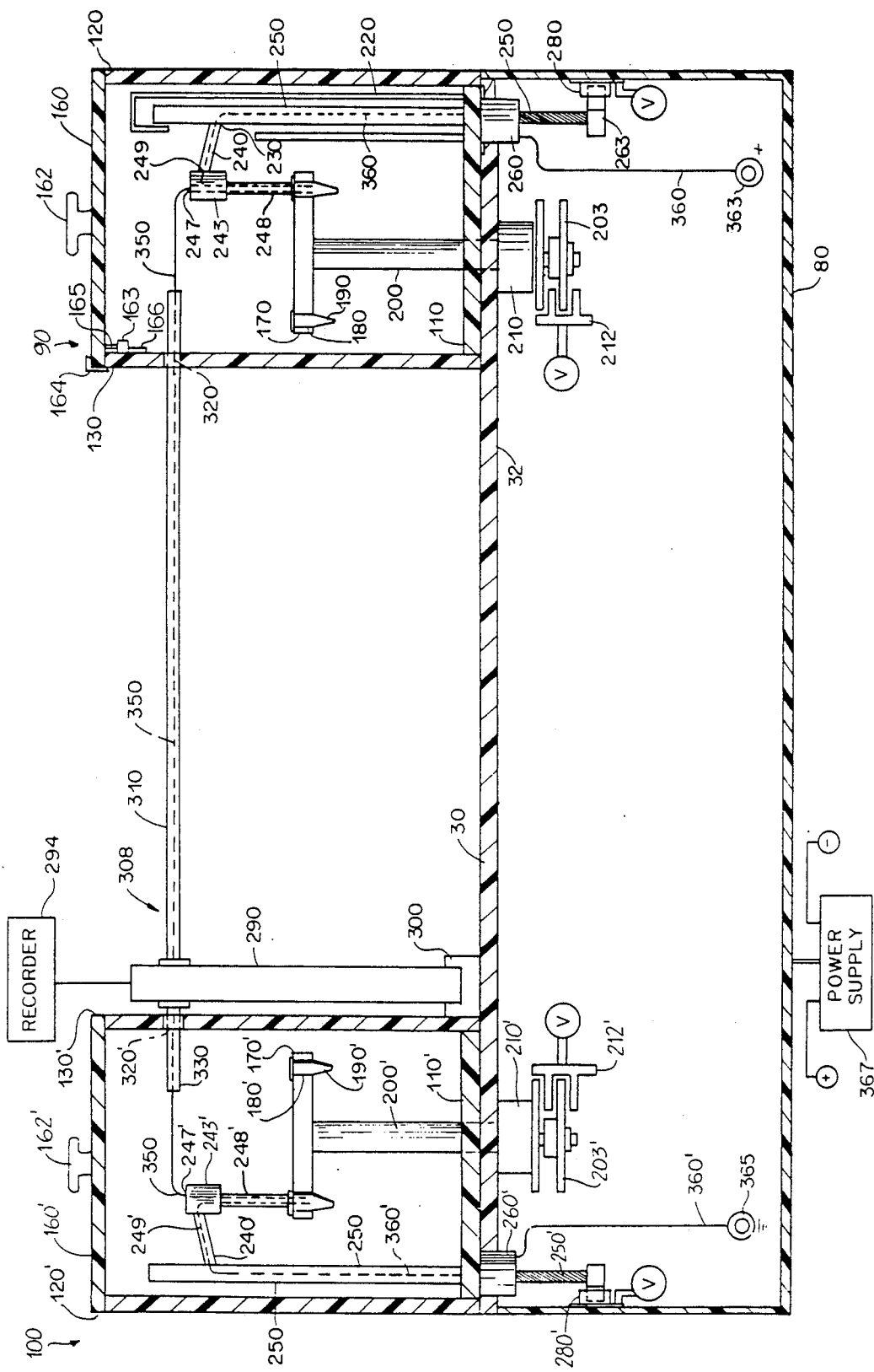
FIG. 2 is a sectional view along the lines 2—2 in FIG. 1.
Figure 3:
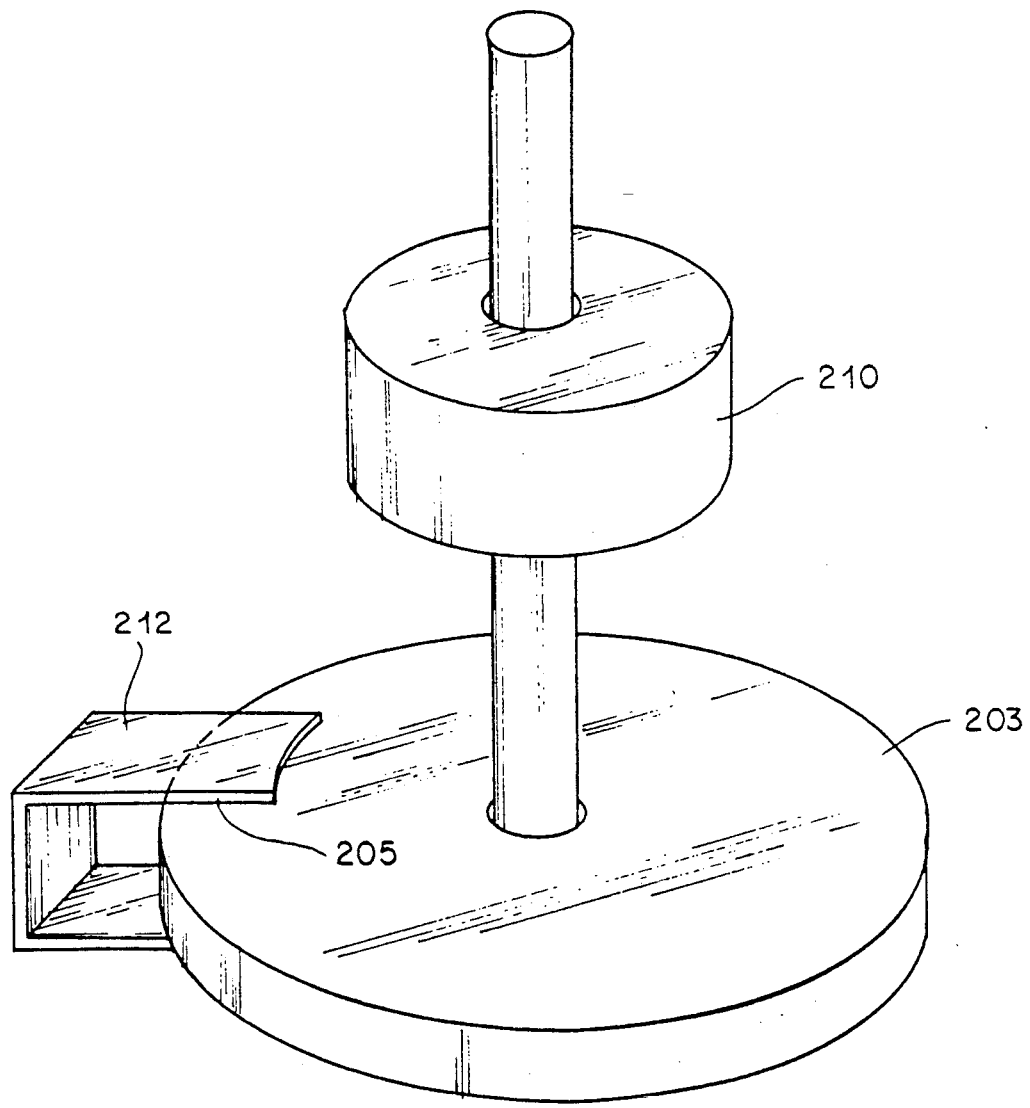
FIG. 3 is a perspective view of a portion of the apparatus shown in FIG. 1.
Figure 4:
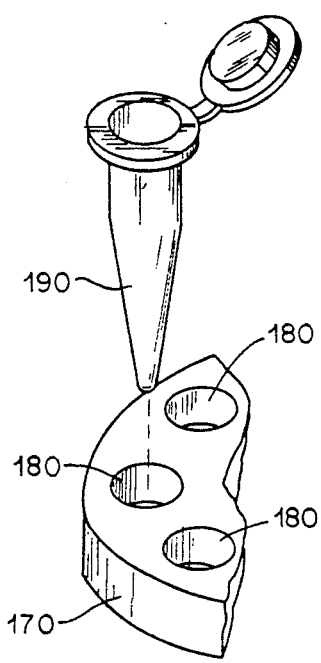
FIG. 4 is a perspective view of a portion of the apparatus of FIG. 1.
Figure 5:
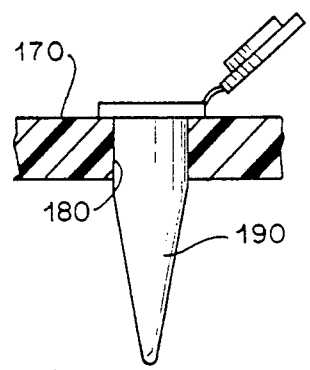
FIG. 5 is a sectional, elevational view of a portion of the apparatus of FIG. 1.
Figure 6:
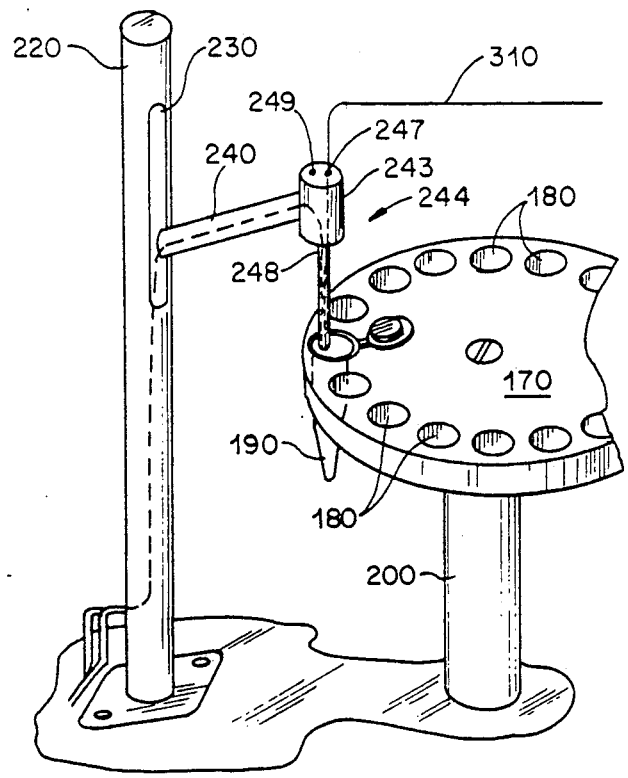
FIG. 6 is an enlarged perspective view of a portion of the apparatus of FIG. 1.

Adjacent to the rotatable table 170, referring to FIGS. 1, 2 and 6, is a hollow, tubular vertical post 220 having an aperture or slot 230 in its side wall. A horizontal arm 240 has one end inside post 220 and secured to a vertical rod 250 which is suitable mounted so that it can be driven vertically up and down. The lower end of the vertical rod 250 or an extension thereof passes through a small motor 260 secured to the lower surface 32 of the top wall 30. The lower end of the rod 250 carries a laterally projecting arm 263 which is positioned to operate with an optical sensor 280 positioned adjacent thereto.

Referring again to the horizontal arm 240, (FIGS. 1, 2, and 6) the outer end thereof terminates in a small solid cylinder 243 which is oriented vertically and is provided with two through-holes 247 and 249 which communicate with a hollow tube 248 which extends downwardly from the solid cylinder in alignment with the holes 180 in table 170 and the sample cups therein. The hollow tube 248 is of a small diameter and is dimensioned so that it can enter a sample cup 190 and extend to about the bottom thereof to enter fluid therein.

The box 100 contains the same apparatus as box 90 as described above. The corresponding parts in box 100 carry the same reference numerals as the parts in the box 90 but primed.

The boxes 90 and 100 include means for applying electrical potential across the apparatus 10. This means includes a first wire electrode 360 having one end secured to a power input terminal 363. (FIGS. 1 and 2) in the rear upwardly in the hollow tube 220 adjacent to the vertical rod 250 and out of the opening 230 in the side wall and through the hole 249 in cylinder 243 down through the tube 248 to the end thereof so that it can rest in a fluid in a sample cup when the apparatus 10 is in operation.

The electrical means also includes a similar wire electrode 360' secured to a power input terminal 365 in the rear wall 50 of the apparatus 10. This electrode follows a similar path through tube 250' and cylinder 243' into the tube 248' associated therewith for ultimate insertion into a sample cup. The electrodes 360 and 360' are preferably of platinum or the like and are adapted to carry the voltages used in operation of the invention. A power supply 367 is provided for connection to terminals 363 and 365 to electrodes 360 and 360' for providing the required voltages. Power supply 367 may also provide whatever other power is needed by the apparatus 10 such as for the motors 210, 210' and 260, 260'. Other auxiliary power supplies may be provided as desired.

In one embodiment of the invention, illustrated in FIG. 2, the power supply 367 may be of such small size that it can be mounted within support member 20 at any suitable location so that the apparatus 10 has its own self-contained power supply which may be manually or computer-controlled.

Figure 7:
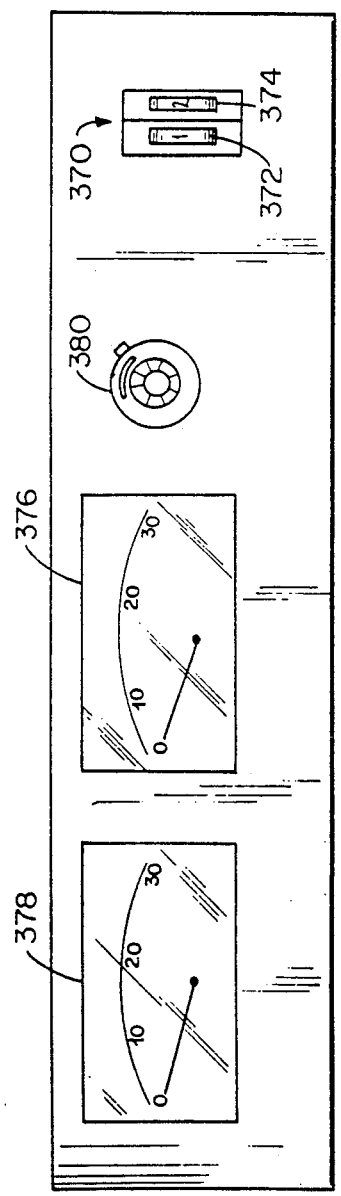
FIG. 7 is a front view of a portion of the apparatus of FIG. 1.

When a built-in power supply is provided, referring to FIG. 7, a voltmeter 376 and an ammeter 378 are secured to the front wall 40 of support member 20 along with a rheostat for adjusting the operating voltage shown on the voltmeter.

Figure 8:
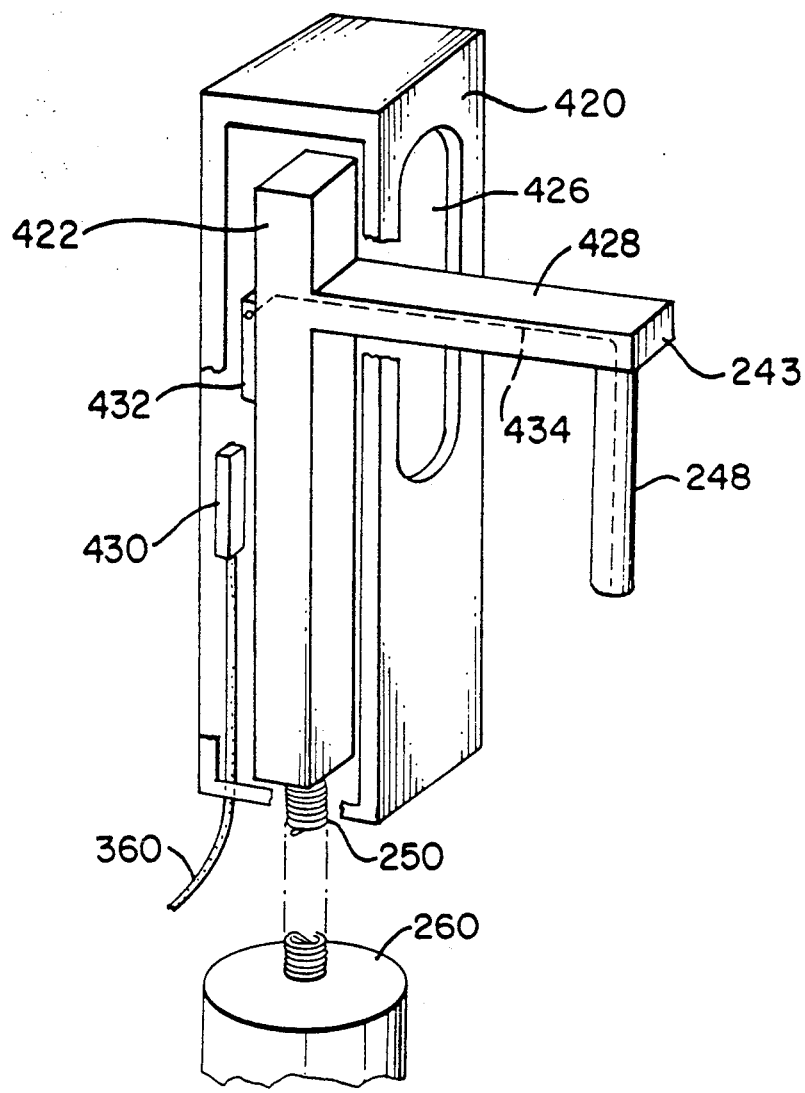
FIG. 8 is a side elevational view of a modification of a portion of the apparatus of FIG. 1 with portions thereof in section.

A preferred structure for the vertical posts 250, 250', to insure electrical safety when high voltage is applied to electrode 360, is shown in FIG. 8. This embodiment for ease of construction includes an outer post 420 and slidable inner post 422 which are both generally square or rectangular in construction. The outer post includes a slot 426 in its side wall and a horizontal arm 428 extends therethrough from the inner post 422. Arm 428 terminates in cylinder 243. The cable 360 comes up from the terminal 363 and runs inside the outer post 420 and terminates in a rigid, relatively large-area flat metallic electrode 430 positioned perhaps half-way up the post to slightly below the slot 426 therein.

Similarly, the slidable inner post 422 carries on its outer surface a relatively large area electrode 432 which is suitably positioned so that when the inner post lowered to operating position, the two electrodes 430 and 432 are in contact with each other. A thin platinum 434 runs from the electrode 432 through horizontal arm 428 and into the cylinder 243 and hollow tube 248 as described above.

Referring to FIGS. 1 and 2 an optical detector 290 for use in detecting material passing through an optical detector 290 for use in detecting materials passing through a capillary tube which extends through the detector is seated on a support frame 300 secured to the top wall 30 of the support member 20 adjacent to the box 100. The apparatus 10 is designed to use a detector known as an on-column detector of the type which uses ultraviolet or fluorescent light in the detection process. Such detectors are made by ISCO of Lincoln, Neb. and EM SCIENCE of Cherry Hill N.J.

For use with the apparatus of the invention 10, modifications of the commercial detectors were made in the cuvette thereof. Other modifications might also be made.

The detector 290 is coupled to other apparatus 294 for providing a record of the detection operation and one such apparatus is the ISCO US-5/V4 absorbance/fluorescence variable-wavelength detector or the EM SCIENCE L-4200/L-4000 UV/visible variable-wavelength detector which include a strip chart recorder and/or an integrator.

A rigid holder 308 is provided for supporting a capillary tube for the apparatus 10 between box 90 and box 100 (FIGS. 1 and 2). This holder comprises a first hollow rigid tube 310 threadedly secured to one end of the cuvette of the optical unit of the detector 290 and supported along its length in a hole 320 in the side wall 130 of the box 90 and extending into the box 90. A second hollow rigid tube 330 is threadedly secured to the other end of the cuvette of detector 290 and is supported along its length in a hole 320 in the side wall 130 of the box 100 and extending into the box 100. The tubes 310 and 330 are aligned with each other and with the optical sensing element located within the detector 290.

Figure 9:
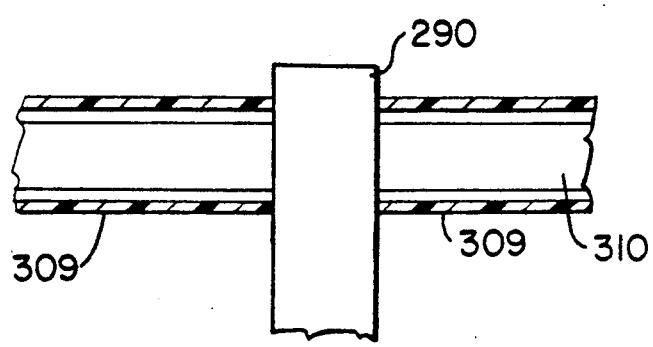
FIG. 9 is a front elevational view of a modification of a portion of the apparatus shown in FIG. 1.

Preferably, the capillary tube holder 308 is provided with surrounding rigid tube 309 (FIG. 9) through which a cooling or heating fluid of any suitable type can be circulated in any suitable manner, to control the temperature of the capillary tube holder and the capillary tube therein.

Figure 12:
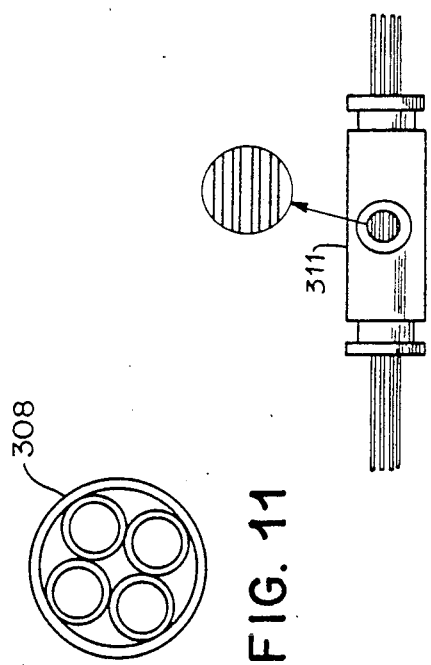
FIG. 12 is a plan view of a portion of a detector used in FIG. 1 with the apparatus of FIG. 11.

The apparatus 10 utilizes a small-diameter, fused silica flexible quartz tube 310 through which ultraviolet light or fluorescent light used in the detector 290 can pass. The capillary tube, as noted above, may have inside diameter in the range of about 25 microns to about 200 microns and a length in the range of about 10 centimeters to about 100 centimeters. The capillary 350 is supported in the hollow rigid holder 308 and extends through the on-column detector 290 and through the optical sensing element or cuvette therein (FIG. 12). At least the portion of the capillary which passes through the cuvette is transparent to the type of light used in the detector. The input end of the capillary 310 in box 90 extends through hole 247 (FIG. 6) in the cylinder 243 and into the tube 248 to the end thereof so that the capillary can be inserted into a sample cup in table 170. The outlet end of the capillary 250 in box 100 extends through hole 247' in the cylinder 243' and into the hollow tube 248'.

Since high voltages are used in operating the apparatus of the invention, it is clear that the capillary tube and the electrodes 360 and 360' should be spaced apart and insulated from each other.

The apparatus 10 includes a timer control 370 for purpose to be described. The timer control is mounted in the front wall of the support member 20 (FIG. 7) and it includes two rotatable control wheels 372 and 374 each of which carries digits 0 to 9. The timer control is used for controlling the time of application of operating voltage to the apparatus 10 described below and it may be manually or computer controlled.

In open-tubular capillary electrophoresis, using potential differences of about 5 to about 30 KV, an electroosmotic flow of buffer is generated in small bore capillaries which transport solute molecules (analytes) toward a detecting system. Charged analytes also migrate with or against this flow, depending on their mobilities and the intensity of the electroosmotic flow. In some cases, it is desirable to eliminate the electroosmotic flow effect and this can be achieved by providing in the carrier medium in the capillary certain substances such as methyl cellulose or certain electrolytes or polyacrylamide gels. The elimination of the electroosmotic flow effect permits charged particle migration due to the effect of applied voltages.

In the following description of the invention, it is assumed that precautions are taken to diminish electroosmotic flow in order to obtain controllable separations.

In general terms in the electrophoresis process as practiced with the apparatus 10, the capillary tube 310 is filled with a buffer solution which has a pH higher than the highest pK of the protein or other constituent in the sample being analyzed. This provides the desired negative charging of the capillary and the sample to be analyzed and the desired resultant flow of negatively charged sample particles toward the end of the capillary at which positive electrical potential is applied. In operation of the apparatus 10, ground potential is applied to electrode 360' and positive potential is applied to electrode 360. The capillary tube is filled with the desired buffer solution and then a quantity of a sample is injected into the high voltage positive (if a positive high voltage power supply is used) end of the capillary tube 350. The components of the sample become electrically negatively charged and each component takes on a different magnitude of charge as determined by the pH of the buffer solution and the migration takes place in the direction of the electroosmotic flow. The charged components of the sample become spaced apart in the capillary tube and with the proper potential applied, the more highly negatively charged components pass more quickly along the capillary through the on-column detector 290. The detector senses the passage of the charged particles and the recorder 284 prints a pulse of each type of charged particle with the pulse representing the position of the particles in the flowing stream and the quantity of the particles therein.

More specifically, in operation of the apparatus 10, the following steps are performed:

1. First post 250 is raised to provide access to the free end of the capillary tube 310, and the capillary tube is filled with buffer solution of the selected pH by connecting, through a plastic tube connector, one end to a suction pump and applying mild suction. To insure proper electrical operation of the buffer solution, it is degassed by agitation and vacuum, ultrasonic methods or by the introduction fo nitrogen or helium absorbs oxygen and as an added advantage prevent bacteria growth. Also, all samples and buffers are filtered through 0.22 micrometer filters to eliminate large particles which may clog the capillaries.
2. Next, with the buffer-filled capillary tube properly positioned in the hallor tube 248, the post 250 and arm 240 are raised and the table 170 is rotated to the position where the first sample cup containing a sample to be analyzed is located beneath the tube and the tube is lowered into the sample in the sample cup.
3. The power supply is connected with its positive output at terminal 363 on electrode 360 and the other end is grounded. The timer 370 is set manually or by a computer-controlled system for the required number of seconds needed to draw electrokinetically a desired quantity of sample into the input end of the capillary and a voltage in the range of about 5,000 to 10,000 volts is applied. After the set number of seconds have elapsed, a quantity of the sample to be tested is present in the input end of the capillary.
4. Next, the voltage is decreased to zero and then the arm 290 is raised and the table 175 is rotated so that the next sample cup containing buffer fluid is positioned under the arm and the arm is lowered so that tube 248 enters this sample cup.
5. Now, the voltage is increased to up to about 30,000 volts and this voltage is applied for perhaps 10 to 40 minutes, depending on the smallest charge assumed to be present on a component of the sample and to insure that the entire sample passes through the capillary. The sample is drawn through the capillary and through the on-column detector 290 to a sample cup at the other end of the capillary. The same operation may now be performed with other samples to be analyzed.

Figure 10:
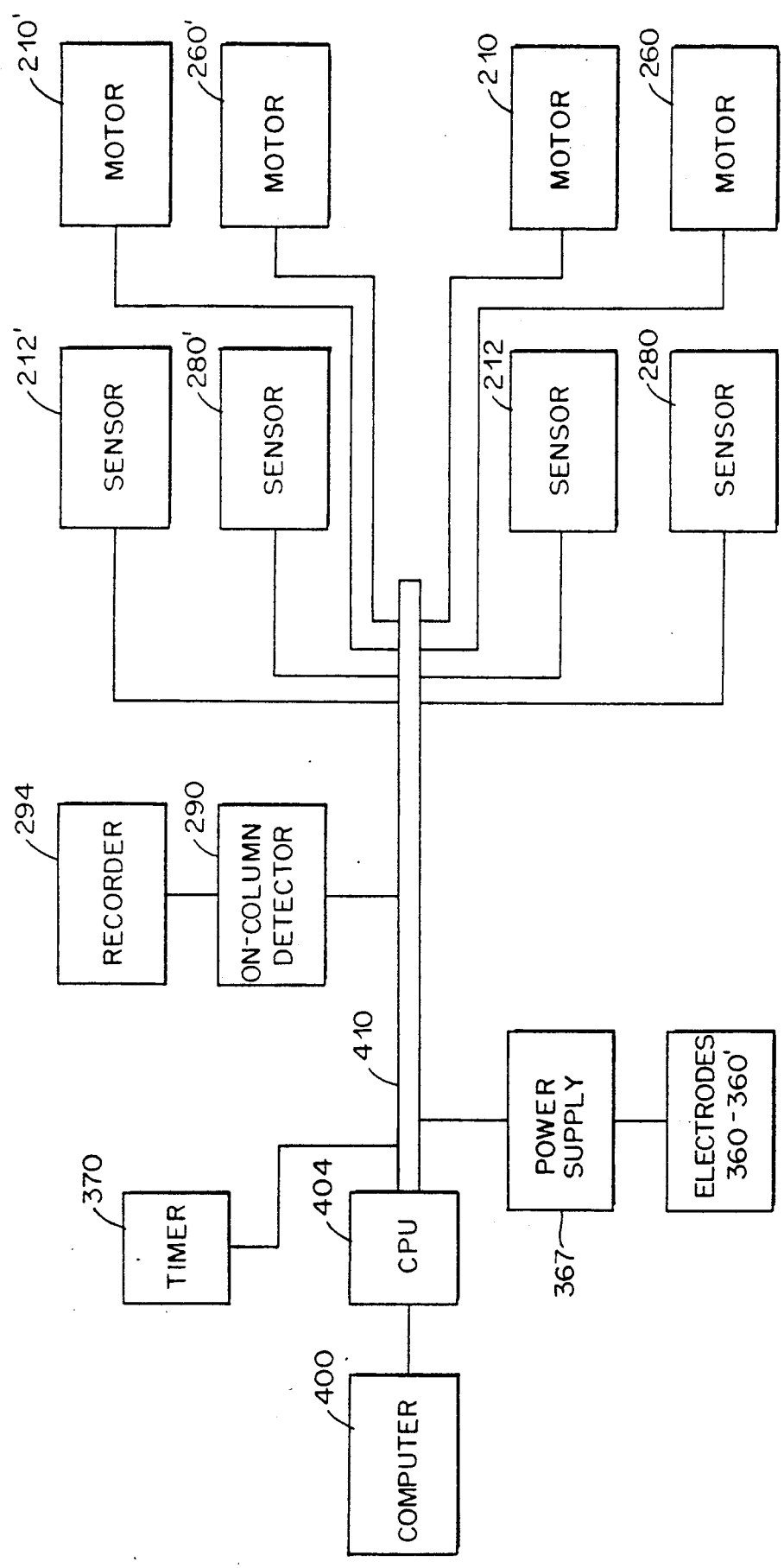
FIG. 10 is a schematic representation of the electronic control system used in the invention.

The apparatus of the invention 10 and the foregoing method are automated and computer-controlled in the system shown in FIG. 10. The apparatus shown in FIG. 10 includes a computer 400 having a central processor CPU 404, and a bus 410 which provides pathways for interconnecting the various operating portions of the invention.

The output of the power supply 367 is connected to the electrodes 360, 360' and it is connected to the bus 410 and to the CPU. The timer 370 is also connected to the bus and the CPU which controls the length of time during which power is applied by the power supply to the electrodes 360 and 360'. As noted above, this can also be done manually.

The rotary motors 210 and 210' and the associated sensors 212 and 212' are coupled to the bus and thus to the CPU. Similarly, the up-down motors 260 and 260' and their sensors are coupled to the bus and the CPU. In addition, the on-column detector 290 is coupled to the bus and to the CPU and to the recorder.

In automatic operation of the apparatus 10 controlled by a program set into the computer 400 and CPU 404, first, power is applied to the components of the system including the up-down motors 260, 260' and posts 250 and 250' are raised to raise tubes 248 and 248' above the tables 170 and 170' to the desired height as set into the program. Next, power is applied to the rotary motors 210 and 210' so that the tables 170 and 170' rotate and the disks 203 and 203' are rotated to a position where the slots 205, 205' therein reach the sensors 212, 212' and complete the light paths across the optical sensors 212 and 212'. This places the tables with a selected first hole 180 and sample cups therein under the tubes 248 and 248'. This is considered the normalized or starting position of the apparatus 10.

Next the operator fills the capillary tube 350 with buffer solution, for example by attaching one end to a suction pump and drawing the degassed buffer solution slowly into the capillary. After the capillary is filled with buffer solution, the end is set in place in the tube 248 or 248' again. At this time, the tube 248 is positioned over the arbitrarily designated first cup and this cup contains the first sample to be analyzed.

If the sample is in the next cup, then motor 210 is energized to move the table a distance controlled by the program which automatically places the next cup, which contains sample, under tube Now, motor 260 is energized to lower the arm 240 and the apparatus including tube 248 into the cup containing sample material. The power supply is manually or automatically turned on to apply a potential of about 5,000 to 10,000 volts to the electrodes 360 with electrode 360' grounded and this potential is applied for the number of seconds set by the timer 370 and estimated to be required.

During this period of time, a quantity of sample is drawn into the end of the capillary tube. At the end of the selected time, the power is either mechanically or automatically turned off and no additional sample is drawn into the capillary tube. Care must be taken to avoid formation of bubbles in the buffer or any other phenomena which may adversely affect the normal passage of current. The analytes in the sample become charged in the buffer solution.

Next, the up-down motor 260 is energized to raise the post 240 and the associated apparatus and the tube 248 is raised above the table 170. Next, the motor 210 is turned on and the table 170 is automatically rotated so that the next cup 180 containing buffer solution is positioned under the tube 248. Next, the motor 260 is energized to lower the post 240 until the motor is stopped by its sensor 263 at just the point where the tip of the tube 248 is at about the bottom of the cup 190 or is suitably positioned within the buffer solution.

Next, the power supply 367 is manually or automatically switched on to apply a positive potentioal of about 30,000 volts to the electrode 360 and this causes the charged components or analytes to flow in the direction of the electroosmotic flow through the capillary tube and through the on-column detector 290. The recorder 194 registers a pulse for each component which passes through it.

As the sample passes through the detector, suitable signals pass through the system to energize the appropriate components of the box 100 to receive the sample and then to rotate the table 170° to another position if such is required.

After the first sample is run, a second sample may be run in the same fashion.

Figure 11:
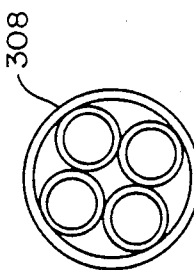
FIG. 11 is a sectional view of a modification of the capillary portion of the apparatus of FIG. 1.

In a modification of the invention, illustrated in FIGS. 11 and 12 a plurality of capillary tubes 310 of the same diameter are provided in the holder 308 and they are operated in parallel, or in a bundle, to provide a larger sample handling capacity. FIG. 12 shows multiple capillaries 310 in the detector cuvette 311.

Figure 13:
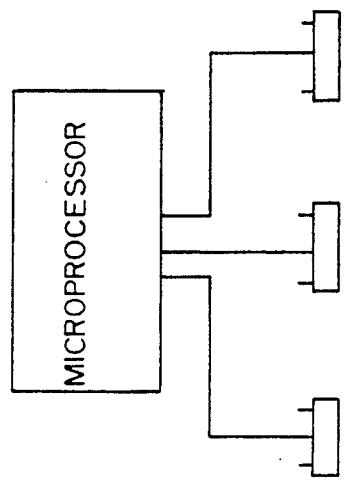
FIG. 13 is a schematic representation of a mode of operating multiple pieces of apparatus of the type shown in FIG. 1.

As illustrated in FIG. 13, the computer and microprocessor can control the operation of several apparatus 10 simultaneously.

With respect to the injection of a sample into a capillary, if desired, the sample may be injected manually or in other suitable fashion. In one arrangement, the cups 190 and 190' can be positioned at different elevations, with cup 190' lower, to permit a quantity of sample or other fluid to flow into the sample end of the capillary.

As a modification of the invention, the apparatus 10 can be adapted to include means by which rather than raising and lowering the posts 250 and 250' and their associated apparatus, it raises and lowers either just specific sample cups or the entire tables 170 and 170'. In this embodiment of the invention, the motors 210 and 210' would be constructed to both rotate the posts 200 and 200' and to raise them and lower them vertically as required to raise and lower the tables 170 and 170'. Alternatively, a separate up-down motor 207, 207' (FIG. 3) would be coupled to the table posts 200, 200'.

Since relatively high voltages are used with the apparatus of the invention, means are provided for disconnecting the electrical power if the operator may be exposed to high voltage. This may occur if the operator removes one of the covers 160 and 160' on the boxes 90 or 100. Thus, as a safety measure in one arrangment illustrated in FIG. 2 with respect to box 90, a switch 163 is positioned inside the box on one of the side walls, e.g. wall 120, and close to the cover 160 and adapted to operate with the cover as a power interlock. Thus, for example, with the switch 163 mounted near the cover, the cover carries a pin or arm which closes the switch when the cover is in place and opens the switch when the cover is removed and thus disconnects the high voltage from the apparatus.

In addition, a clamp 164 is coupled to each of the covers 160 and 160' and is hinged to a side wall and positioned to engage the cover. The clamp must be moved before the cover can be removed. Thus, if desired, the switch 163 may be mounted so that it is operated by the clamp or if desired there may be an auxiliary switch (not shown) associated with the clamp.

All of the electrical connections to the switches and power supply used with the apparatus of the invention are not shown, since the connection of switches into the circuit can be easily accomplished by those skilled in the art. The lead 166 represents connections from the switch to the power supply circuit.

It is noted that the use of small diameter capillaries (25-200 microns) reduces the magnitude of temperature (Joule heat) differences within a capillary and minimizes the zone spreading effects usually found in larger diameter capillaries greater than 200 microns.

Figure 14A:
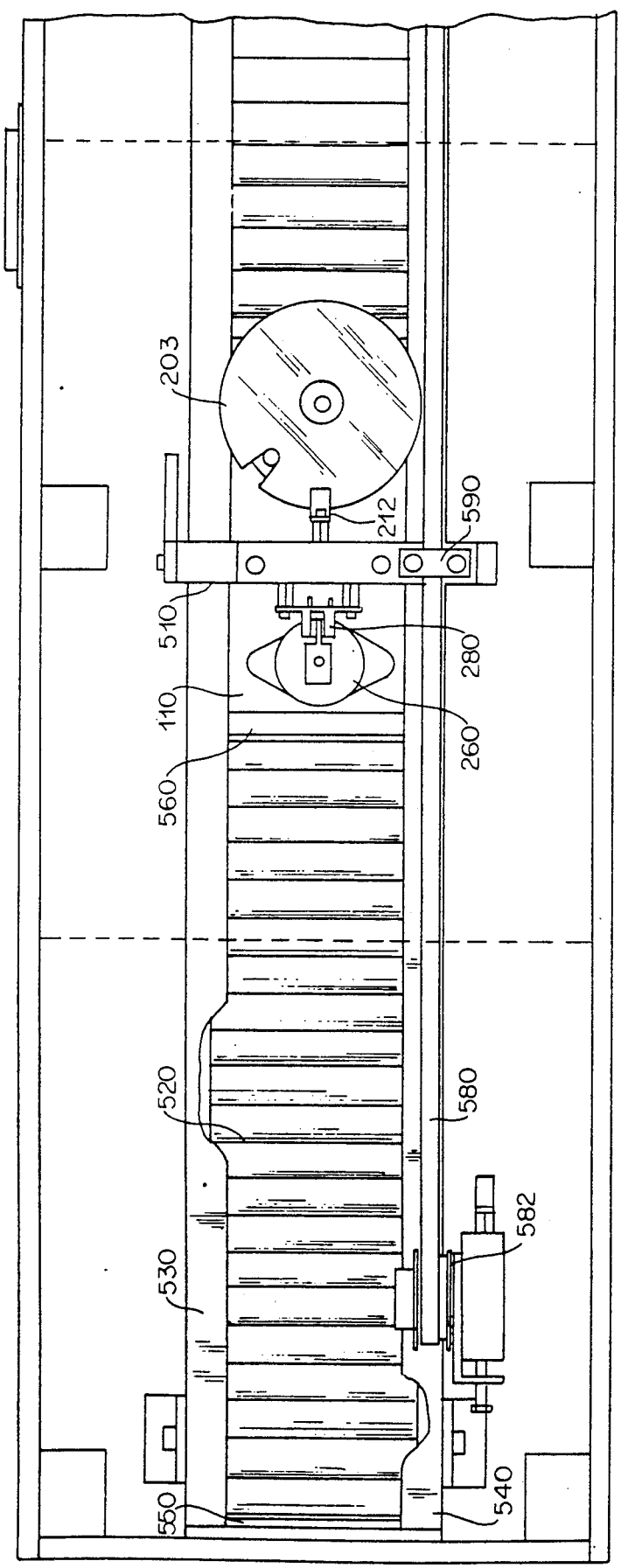
FIGS. 14A and 14B together are a bottom view of a modification of the base support of the invention.
Figure 14B:
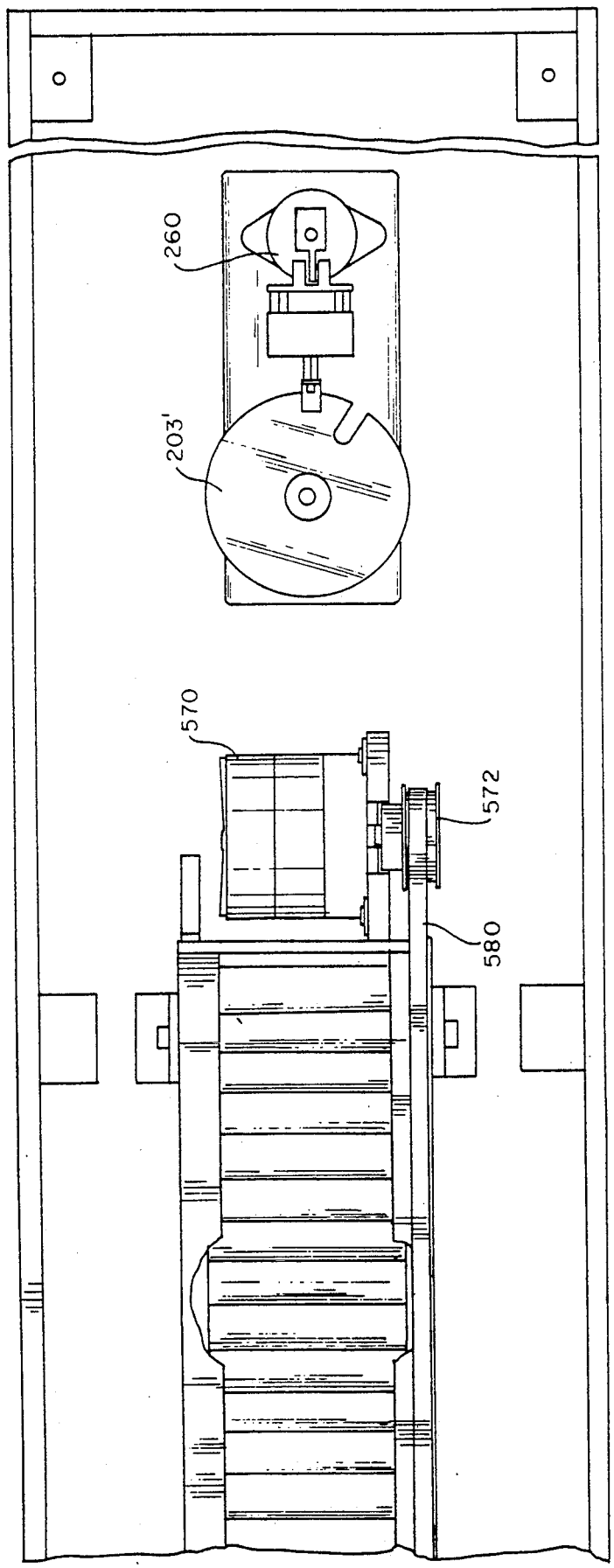

In a modification of the invention shown in FIGS. 14A and 14B and partly in FIG. 1, the box 90 and the parts carried thereby are adapted to slide on the top wall 30 of the support member 20 so that the space between the two boxes 90 and 100 can be adjusted to permit operation of the apparatus with capillary tubes of different lengths.

In this embodiment of the invention, the top wall 30 of the support member 20 is provided with a slot 500 over which the base of the box 90 is positioned. The motors 210 and 260 are secured to the lower surface 32 of the base 110 of the box 90 and beneath the slot 500, and in effect inside the base of the apparatus. Referring to FIGS. 14A and 14B, a vertical insulating plate 510 is secured to the lower surface of the base 110 and extends downwardly therefrom. This plate 510 is disposed between the two motors 210 and 260 and on one surface it carries the sensor 212 for the motor 210 and on the other surface it carries the sensor for the disk carried by the motor.

In order to block the slot 500 so that foreign material cannot fall into the support member, a bellows type member 520 is secured in place beneath the top surface of the support member. To support the beliows, a container is provided made up of two L-shaped elongated strips 530 and 540 which are secured to the lower surface of the support member 20 with two end plates 550 and 560 completing the container.

A motor 570 for driving the box 90 is secured to the lower surface of wall 30 of support member 20. The motor 570 carries a drive wheel 572 which is coupled by means of a drive belt 580 to a second wheel 582 located remotely therefrom. Motor 570 is positioned near the end of the wall 30 beneath box 100 and the wheel 582 is positioned near the opposite end of the wall 30 beneath of the box 90. Wheel 572 is suitably supported on the wall 30 or another wall of the support member 20. The drive belt 580 is secured to the vertical plate 510 by means of a clamping plate 590 with the belt between the vertical plate and the clamping plate. With this coupling arrangement, when the motor 570 is turned on, it causes the belt 580 to move the vertical plate 510 and the base 110 fo the box 90 to which it is secured. As the motor drives the box 90 back and forth, the bellows 520 compresses and expands as required to maintain the slot 500 covered.

Figure 15:
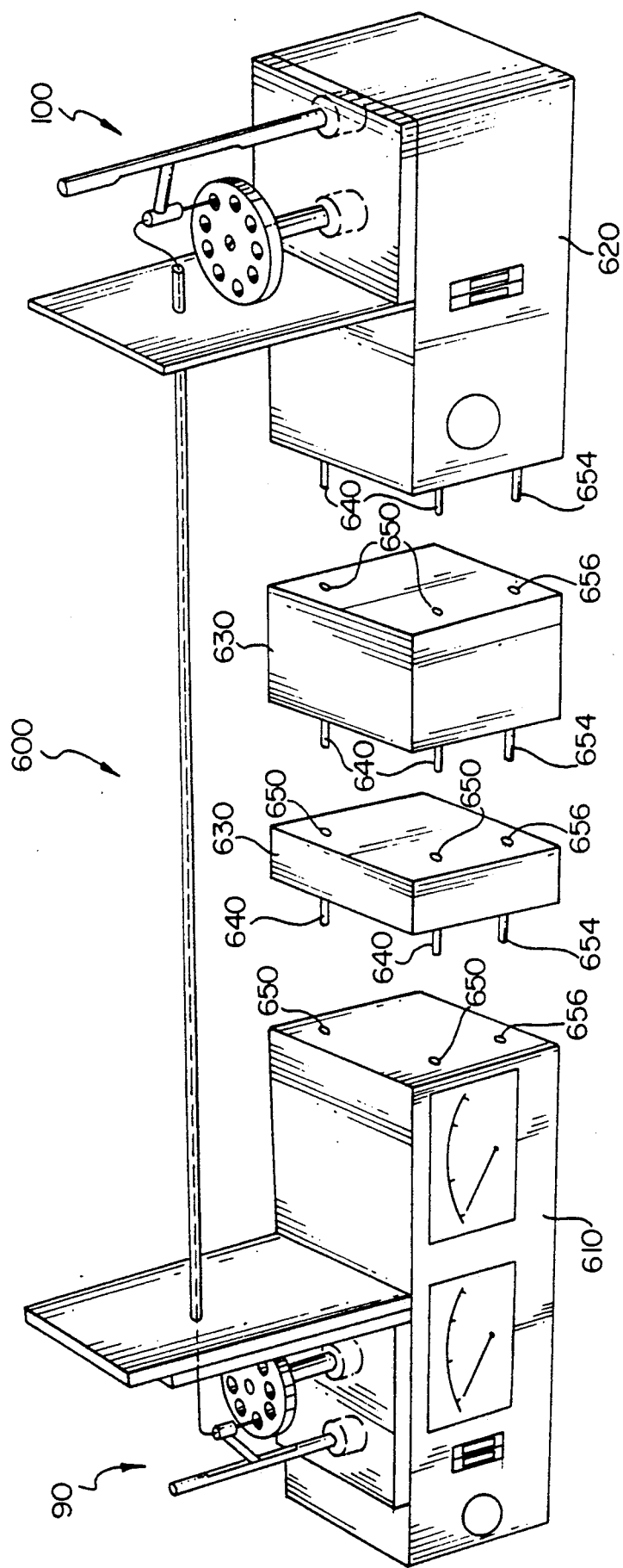
FIG. 15 is perspective front view of a modification of the invention.

A modification of the foregoing embodiment of the invention is illustrated in FIG. 15. In FIG. 15, capillary electrophoresis apparatus 600 is contructed in modules or sections which can be readily assembled and disassembled to vary the length of the apparatus. Thus, as illustrated in FIG. 15 the apparatus includes end sections 610 and 620 including the boxes 90 and 100 and their associated apparatus and auxiliary sections 630 having the same size and shape as the end sections so that all sections blend together. The auxiliary sections 630, in any desired number, can be inserted between the end sections with coupling being achieved in any suitable manner. In one coupling arrangment, the various sections 610, 620 and 630 may carry pins 640 in their end surfaces which enter holes 650 in the adjacent end surfaces of sections to which they are to be coupled.

In the apparatus shown in FIG. 15, the required electrical connections are made in any suitable manner. For example, the power supply and the controls therefore may all be mounted in one end section, or if desired a power supply and controls may be provided in each end section. In addition, if desired, means such as pins 654 and sockets 656 may be provided in the end surfaces of each section so that when sections are coupled together electrical connections are made automatically between the adjacent contacting surfaces at the same time.

The apparatus 600 has the advantage of simplifying the handling of the various modules. The carrying or shipping of several small modules is more convenient than carrying or shipping a single relatively large apparatus. In addition, the auxiliary sections permit the apparatus to operate with capillary tubes of different lengths.

Figure 16:
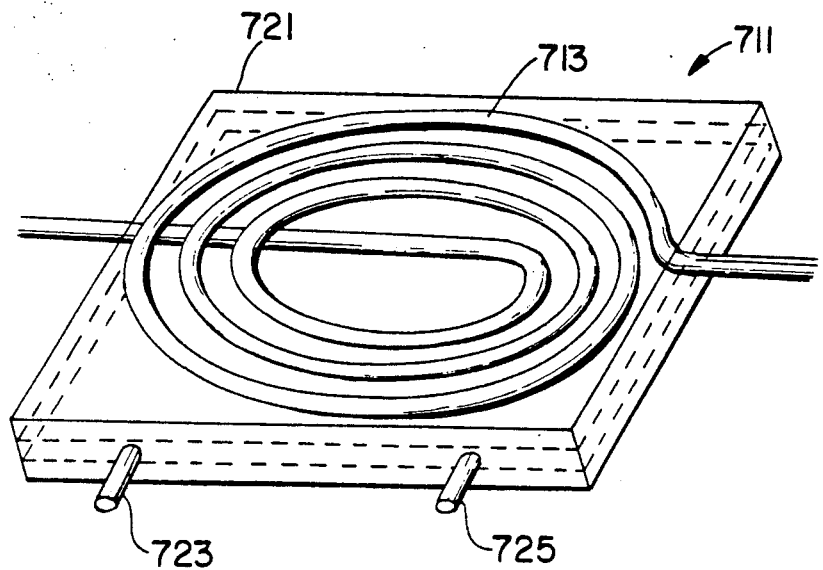
FIG. 16 is a perspective view of a modified capillary cartridge usable with the apparatus of the invention.

The apparatus of the invention may also use a modified capillary which, as shown in FIG. 16, comprises a capillary cartridge 711. The cartridge includes a capillary cassette which comprises a coiled capillary tube 713 embedded in a body of metal, glass, plastic or the like. In coiled form, the capillary tube may be of any suitable length and it may contain various chemistries. The capillary cassette is held in a housing 721 made up of two plates of metal, glass, plastic or the like coupled by screws or the like. A temperature control fluid, which can be heated or cooled, can be circulated through the housing by way of inlet and outlet tubes 723 and 725. It is noted that the capillary cassette can be easily removed from the housing 721 and replaced by another cassette of different size or other characteristics.

The utility of the capillary assembly 711 as a readily replaceable cartridge which can provide capillaries of different lengths and chemistries will be clear to those skilled in the art. A mounting arrangement for the capillary assembly or cartridge 711 is illustrated in FIG. 17.

In a modification of the invention the electrical apparatus is modified so that operating voltages can be pre-set so that by operating a three position switch, the desired pre-set low voltage can be applied to draw sample into the capillary and then the pre-set high voltage can be applied to cause the sample to pass down the capillary. In the third position, zero voltage is applied, the system is off and no current flows.

Figure 17:
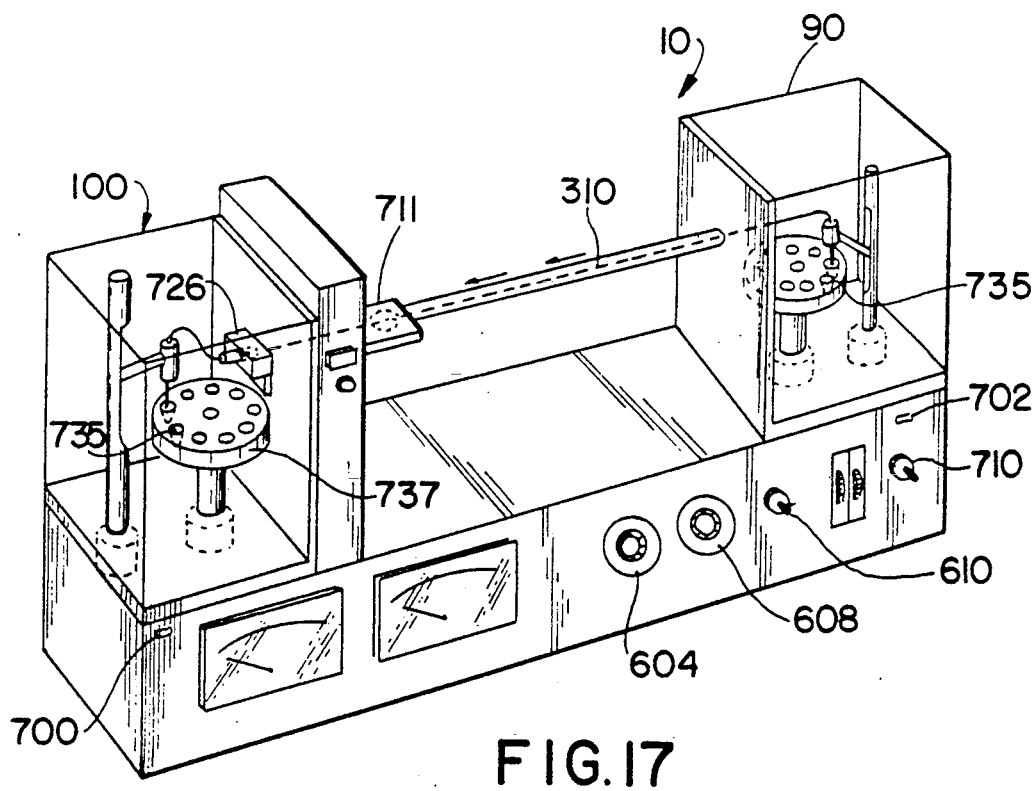
FIG. 17 is a perspective of apparatus embodying modifications of the invention.
Figure 18:
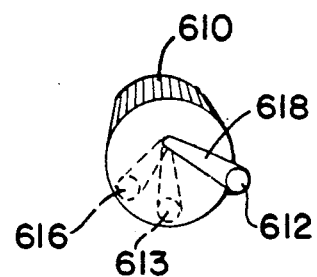
FIG. 18 is a perspective enlarged view of a switch used with the apparatus of FIG. 17.

In this embodiment of the invention, as illustrated in FIGS. 17 and 18, the front panel of the capillary electrophoresis apparatus 10 described above is modified to include a first pontentiometer 604 which is connected to the power supply in the apparatus and is adapted to be set to a selected low voltage and a second potentiometer 608 is connected to the apparatus power supply to be set to a selected high voltage. A single, three-position control switch 610 for applying the voltages set in the potentiometers, in operation of the apparatus, is also mounted on the front panel accessible to the operator. The switch 610, which is shown schematically in FIG. 18 includes a switch arm 618, a low voltage terminal 616, a high voltage terminal 612 and a zero voltage terminal 613.

Thus, in operation of the apparatus shown in FIGS. 17 and 18, when it is desired to draw a sample into the capillary 310 by the application of low voltage across the capillary, the switch 610 is set to terminal 616 to apply the low voltage set by potentiometer 604 across the capillary. This operation usually requires seconds of operating time. When it is desired to apply voltage to cause the sample to flow down the capillary tube, then switch 610 is set to contact terminal 612 to apply the high voltage set by potentiometer 608. This operation usually occupies minutes of time. Switch 610 may be embodied in the computer control system, if such is provided, for automatic operation. The terminal 613 of the switch applies zero voltage so that the system, in effect is turned off and no current flows.

Figure 19:
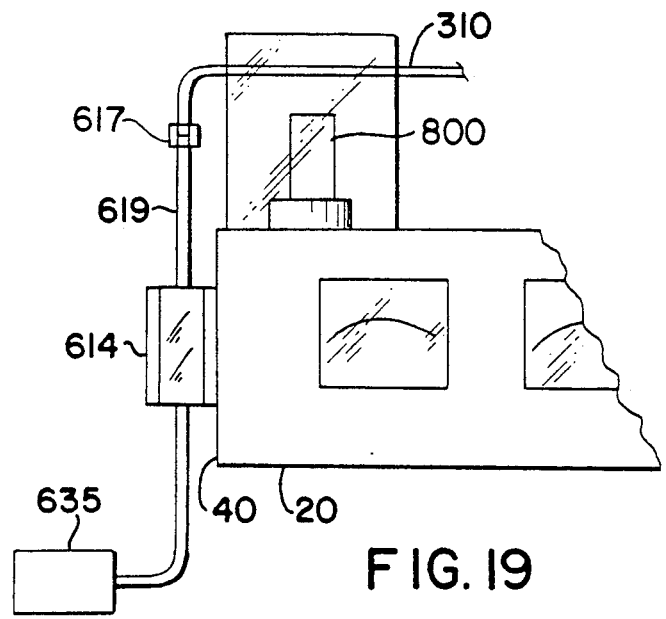
FIG. 19 is a front elevational view of a portion of apparatus of the invention illustrating a modification thereof.

In another modification of the invention illustrated in FIG. 19, a magnifying glass 614 is provided coupled to the capillary tube 310 to permit the operator to observe the flow of buffer solution into and along the capillary and to determine whether gas bubbles are present in the buffer solution. It also permits the operator to determine whether there is normal flow of liquid through the capillary tube. If the flow is very slow or if there is no flow at all, this is an indication of a non-functional column, probably due to blockage of flow because large macromulecules or aggregates are adsorbed on the walls of the capillary or because salt solution has evaporated and aggregates of salt have formed a wall-like interface which stops the normal flow of fluid.

In the modification shown in FIG. 19, the magnifying glass 614 is mounted on an end wall 40 of the housing 20 so that it is accessible to the user. Capillary tube 310 has its left end coupled through a plastic connector 617 to a connecting tube 619 of metal, glass plastic or the like behind the magnifying glass to a vacuum or peristaltic pump 635 and the flow of buffer solution or other fluid therethrough can be observed.

Figure 20:
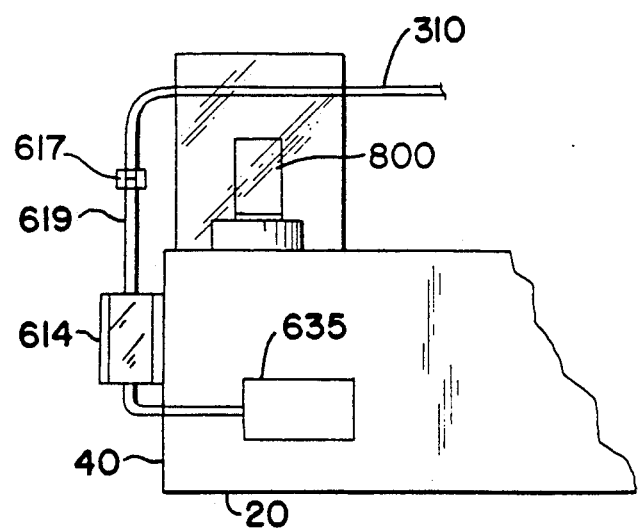
FIG. 20 is a front elevational view of a modification of the apparatus shown in FIG. 19.

In a preferred arrangement, the vacuum or peristaltic pump 635 is a miniature pump which can be mounted within the housing 20 as illustrated in FIG. 20.

After the capillary tube has been filled, tube 619 is removed and the capillary is set in its operating position in the holder described above as shown in FIGS. 1 and 17 or in any other selected apparatus.

In FIGS. 19 and 20, a beaker 800 is shown at the outlet end of the apparatus to receive samples from the capillary for analysis purposes.

The porous glass joint assembly developed for electrochemical detection can be used to collect samples and to calculate the electroosmotic flow. As mentioned above, the application of positive high voltage generates a bulk flow of buffer and analytes in the direction of the grounded electrode.

In another modification of the invention, it is possible to calculate the electroosmotic flow in two different ways. One way is to measure the time to generate a drop at the tip of the detection capillary (the capillary tube after the porous glass joint). Then under a microscope the drop is aspirated by capillarity into a piece of capillary column. Since the distance between the two meniscuses formed can be measured by a caliper, the total volume loaded into the piece of capillary tube can now be calculated with the formula of the volume of a cylinder, knowing the internal diameter of the capillary tube (see below).

Figure 21:
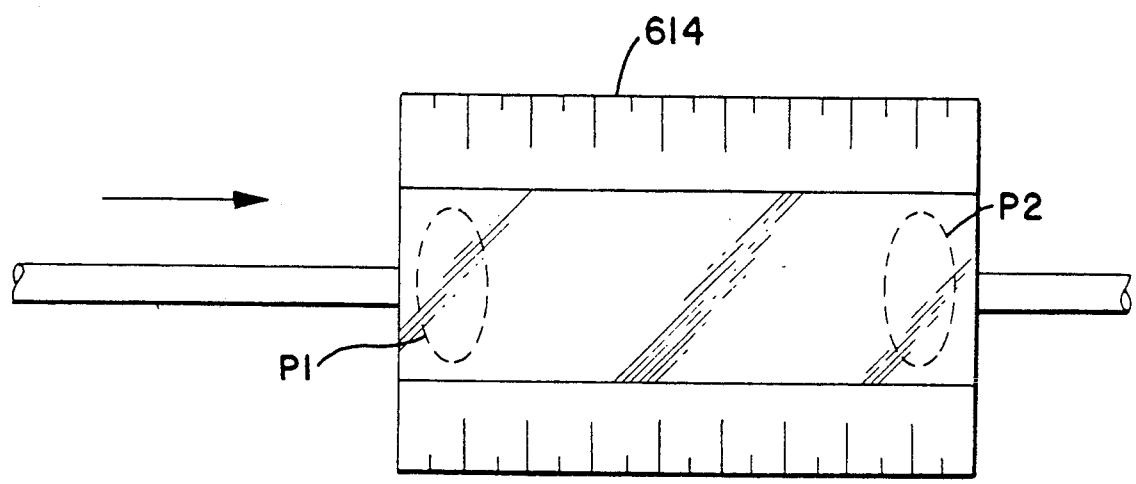
FIG. 21 is a front elevational view of a portion of a capillary tube and magnifying glass used to analyze electroosmotic flow.

It is also possible to measure the electroosmotic flow, referring to FIG. 21, by observing the meniscus formed by the sample with the magnifier 614 which, for this mode of operation is a high power magnifying glass, or microscope or the like located at the terminal end of the detection capillary 727. When electroosmotic flow takes place in the system, if the distance that the meniscus travels between two points (P1 and P2) is known, one can calculate the volume of the sample by using the equation for a cylinder:

$$V = \pi \times (d^2/4) \times 1$$

where V=volume of cylinder, $\pi$=constant=3.1416, d=diameter of the cylinder, and I=the distance between the two points (P1 and P2). In addition if the time needed of the meniscus to travel between the two points in the capillary tube 727 is known, one can calculate the electroosmotic rate of flow by using the equation:

Electroosmotic flow = V/t where V = volum of the cylinder, and t = time needed of the meniscus to travel between points P1 and P2.

The electroosmotic flow for several sets of system parameters is shown in the following Table:

TABLE

Theoretical Determination of the Injection Volume and the electroosmotic Flow Using Fused Silica Capillary of Various Internal Diameters. The Results were Based on Values Determined Empirically with a 75 μm × 100 cm Capillary Column for a Meniscus Migration Time of 60 Seconds. The Applied Voltage was 10 KV (100 V/cm)

| Internal Diameter (μm) | Total Net Volume (μl) | Volume of Injection (nl/60 sec) | Volume of Injection (nl/15 sec) | Electroosmotic Flow (nl/mm/ × $10^3$) |
|---|---|---|---|---|
| 25 | 0.5 | 1.68 | 0.42 | 8.3 |
| 50 | 2.0 | 6.72 | 1.68 | 33.3 |
| 75 | 4.4 | 14.80 | 3.70 | 73.4 |
| 100 | 7.9 | 26.54 | 6.64 | 131.6 |
| 200 | 31.4 | 105.50 | 26.38 | 523.3 |

This computation is made once for the system parameters, i.e., constant temperature, constant buffer composition, constant capillary column dimensions, constant voltage and amperage pulses, etc.

Alternatively, the distance and the time that the meniscus travel between points P1 and P2 can also be calculated using an electronic sensor system.

Figure 22:
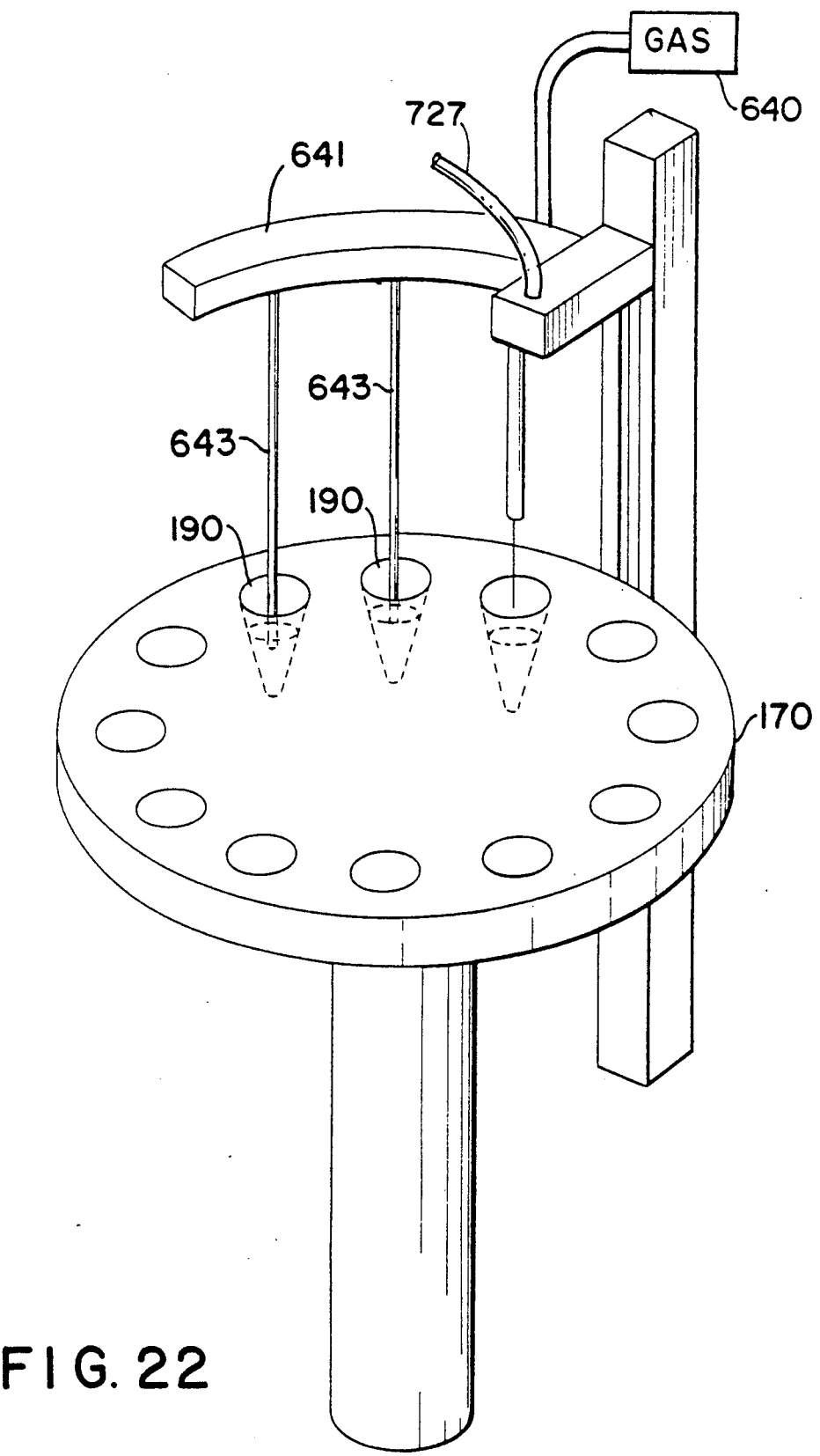
FIG. 22 is a perspective view of a modification of apparatus embodying the invention.

In still another modification of the invention used for degassing the buffer solution, illustrared in FIG. 22, a source 640 of an inert gas such as helium, nitrogen, argon or the like is provided coupled through a manifold 641 and tubes 643 which extend vertically from the manifold 641 to the rotatable table 170. The presence of bubbles in the capillary tube will stop the flow of electrons and the system will not work. Thus degassing of buffers and samples is essential. As the table 170 is rotated the degassing gas is fed into each of the sample cups 190. The microinjector tubes 643 carry small amounts of controllable quantities of gas in order to perform the degassing system as gently as possible without disturbing or contaminating the sampel under study or the buffers necessary for the electrophoresis operation.

Figure 23:
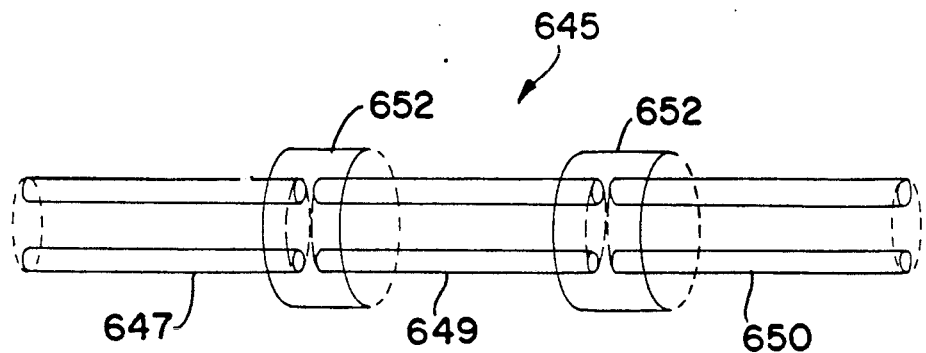
FIG. 23 is a modification of the capillary tube used with the invention.

In another modification of the capillary tube used in practicing the present invention, referring to FIG. 23, a capillary tube 645 includes several portions or segments of capillary 647, 649 and 650 each of which may have a different internal coating. The various coatings are selected to prevent macromolecules adsorption to the capillary walls and for separating the components of a sample whereby more efficient sample analysis can be achieved. Silane derivatives are one of the suitable coating materials. The coating materials used in this modification of the invention may be coated directly on the inner wall of the capillary or it may be provided in bulk form. In bulk form, masses of the chemicals would be inserted in the capillary by themselves or coated on an insulating support body of some kind such as spheres or the like.

The adjacent ends of the tube portions may be butted end to end and coupled together by sleeves 652 which ar secured by a suitable cement such as epoxy to the outer wall of the capillary portions.

Figure 24:
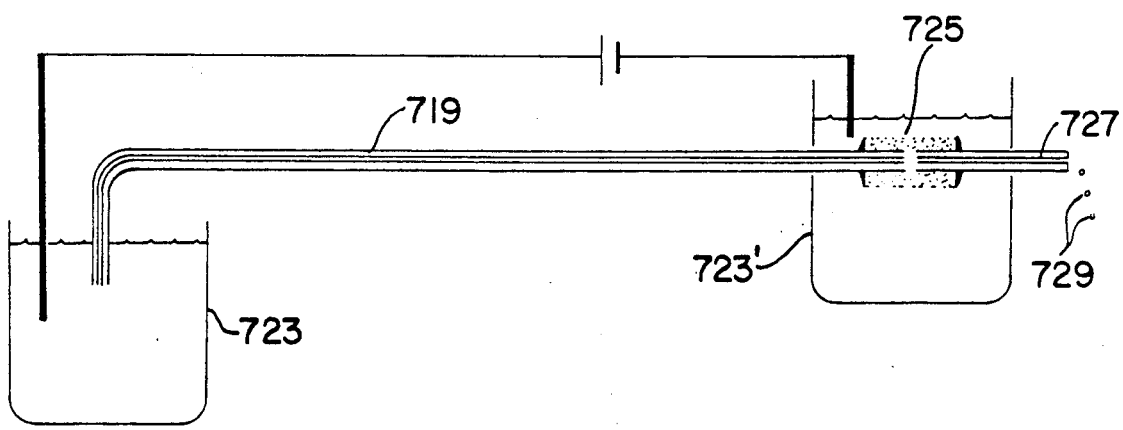
FIG. 24 is a front elevational view illustrating additional apparatus which can be used in the apparatus of the invention.

In another modification of the invention illustrated schematically in FIG. 24, the inlet end of a capillary tube (separation capillary) 719 is in a container 723 of buffer solution and the outlet end (detection capillary) is inserted into a porous glass sleeve 725 placed in a container 723' of buffer solution. A fused silica capillary tube 727 extends from the end of the capillary 719 out of the buffer container and samples flow as droplets out of the end of the capillary tube where they are recovered.

The porous glass tube 725 is a selective membrane which allows ions to escape but the samples to be analyzed pass through the tubing to be collected.

Figure 25:
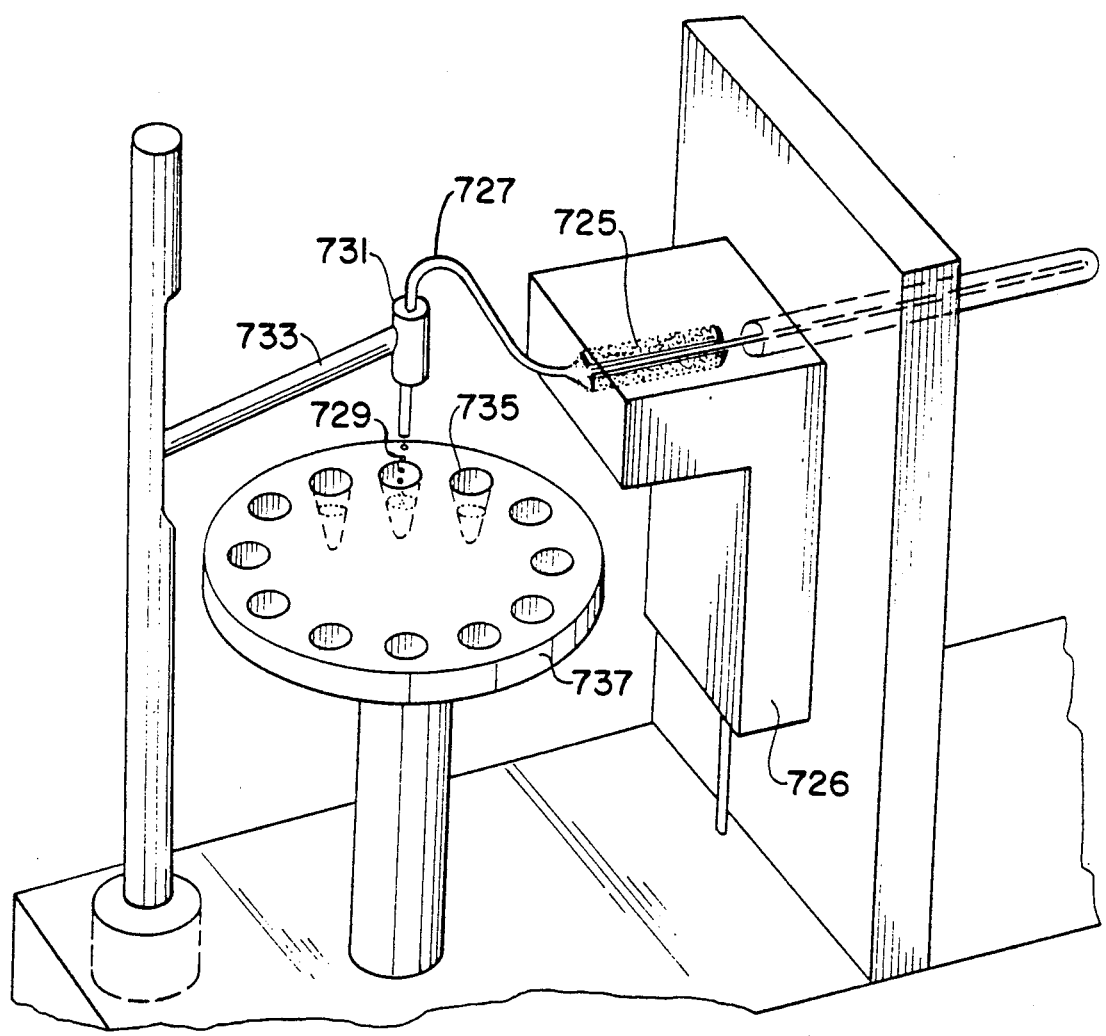
FIG. 25 is a perspective view of a modification of the invention used with some of the apparatus of FIG. 24.

The principles of this invention, used originally for insertion into the open end of the detection capillary of a carbon fiber electrode for electrochemical detection of the solute zones, can be used to provide a fraction collector. As illustrated schematically in FIG. 25, the free end of the capillary tube 727 is directed through a vertical holder 731 coupled to an horizontal arm 733 and positioned over the sample cups 735 in rotatable table 737. In operation of the apparatus shown in FIGS. 17 and 25, high positive potential is applied to an electrode in sample cups 735 in box 90 (autosampler or autoinjector side) and ground potential is applied to an electrode in buffer container 726 (fraction collector side). Since ground potential is in the buffer in container 726, there is no potential and no buffer is required in the sample cups 735 in the table 737 in box 100 and these portions of the overall apparatus can be handled without concern for electrical shock.

Figure 26:
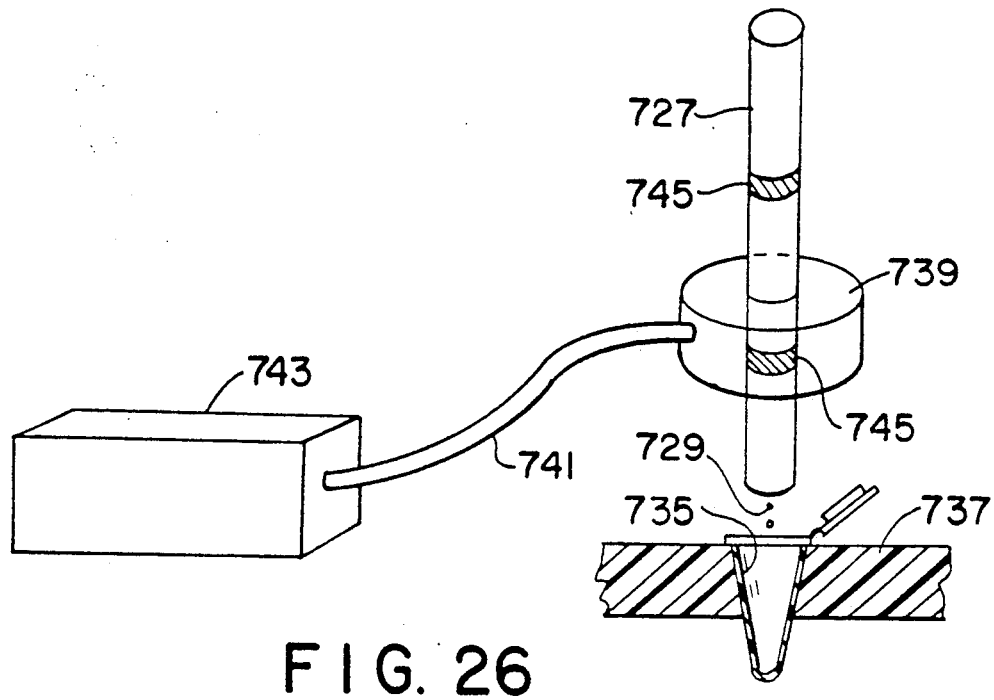
FIG. 26 is a perspective view of a modification of the apparatus of FIG. 25.

In still another modification of the invention last described and illustrated in FIG. 26, a light sensor 739 is coupled to the end of the tube above the rotatable table and an optical glass fiber 741 or the like is coupled from the sensor to a detector 743. With this apparatus, the sensor senses the passage of a sample 745 and this is detected by the detector which is used to determine when the table should be rotated so that a single can be deposited in each sample cup 735.

While the method of operating the apparatus 10, as described above, is satisfactory for many applications and suitable sensitivity is achieved, another method of operation provides improved spectrum analysis and greater ability to identify samples by providing complete spectral analysis. Changes in wavelength increments as little as 1 or 2 mm can be used in order to maximize sensitiviy and cover the entire spectral range.

Figure 27:
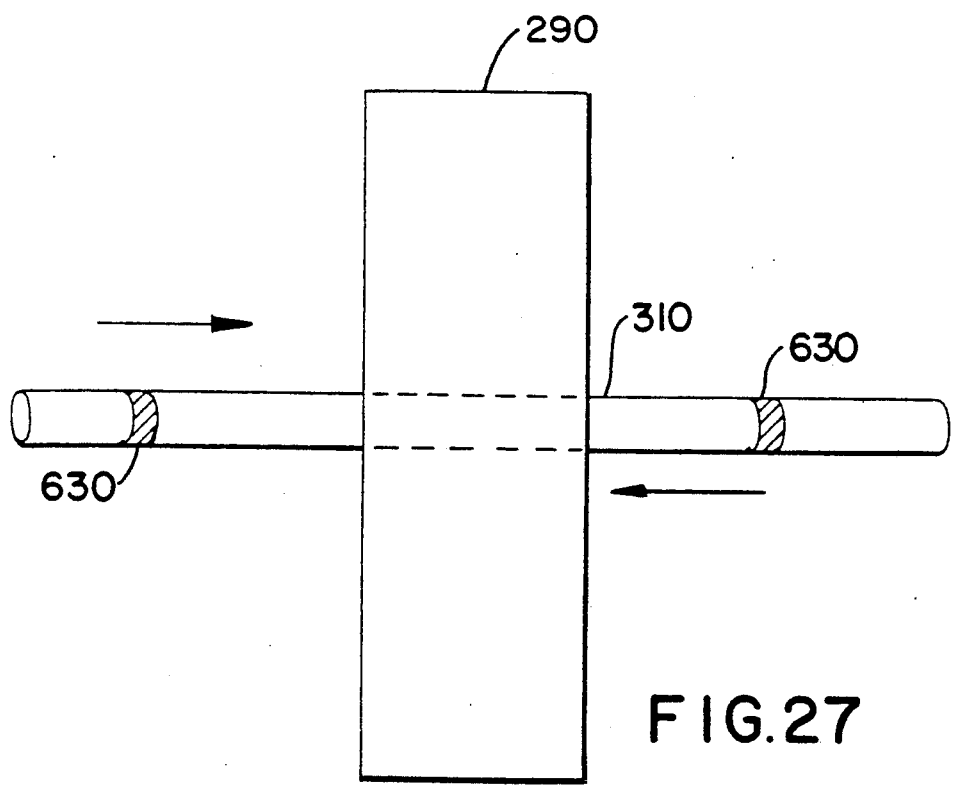
FIG. 27 is a front elevational view of a portion of the apparatus of the invention illustrating a mode of operation thereof.

In this mode of operation illustrated in FIG. 27, the detector is set for a first wavelength of operation and, after a sample 630 flows down the capillary tube to the left to the detector 290 and passes through the detector and provides an output pulse from the detector at the first wavelength, the high voltage polarity is reversed and the direction of the flow of the buffer is reversed, therefore the direction of the sample is reversed, and the sample passes to the right through the detector again, with the detector set a second wavelength. This causes a second pulse to be provided by the detector. Now, the polarity is reversed again and the sample flows is in the original direction to the left and provides an output with the detector set to provide a third wavelength of light. This operation of potential reversal and cyling of the sample back and forth is repeated, at different detector wavelengths of light until a series of pulses is obtained which, when plotted provides two peak wavelengths, with the second peak providing accurate identification of the sample. Almost every pure substance provides such as series of pulses to permit identification thereof.

Figure 29:
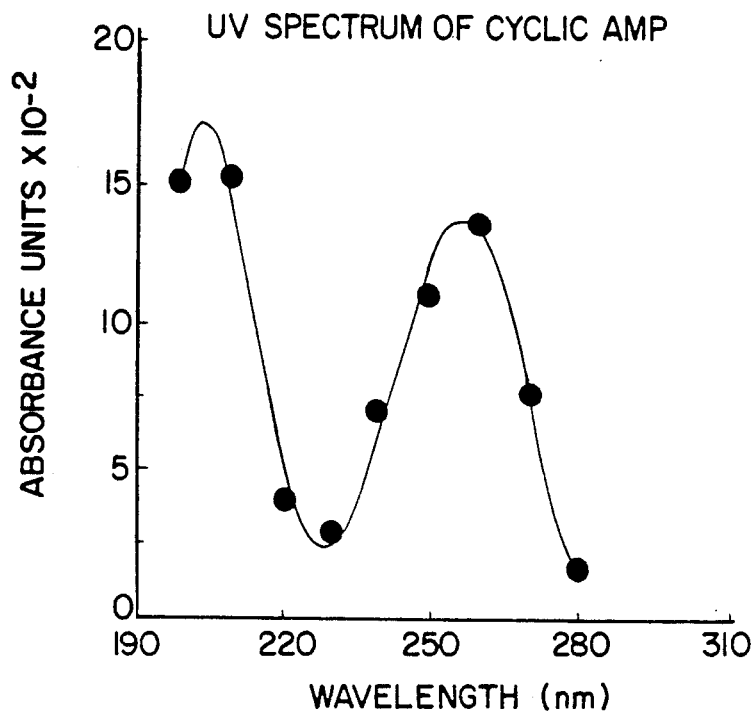
FIG. 29 shows a curve derived from the pulses of FIG. 28.
Figure 28:
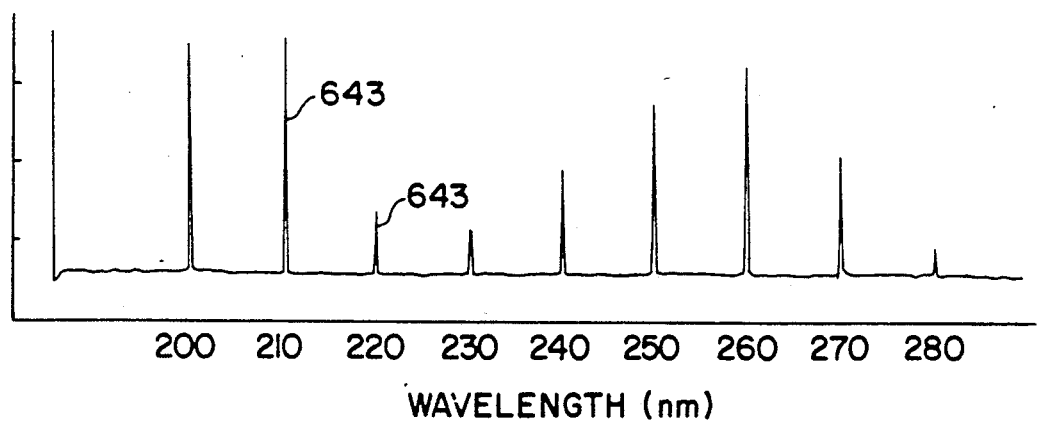
FIG. 28 shows pulses detected by the method of FIG. 27.

A typical series of pulses 643 which might be obtained to provide a complete spectrum for a sample is illustrated in FIG. 28 along with a plot of wavelength versus absorbance, illustrated in FIG. 29.

Lights or lamps 700 and 702, shown in FIG. 17 on the front panel of the apparatus can be used to indicate in which direction flow is taking place at any instant. In addition, a switch 710 is provided for reversing the high voltage polarity to achieve the cycling operation described above.

After many injections of samples, particularly those containing substances which have a tendency to stick to the walls of the capillary column such as serum or other biological fluids, it is necessary to restore the capillary column. Since commercially available fused-silica capillaries are inexpensive, one way to restore the capillary column is to replace it entirely.

Figure 30:
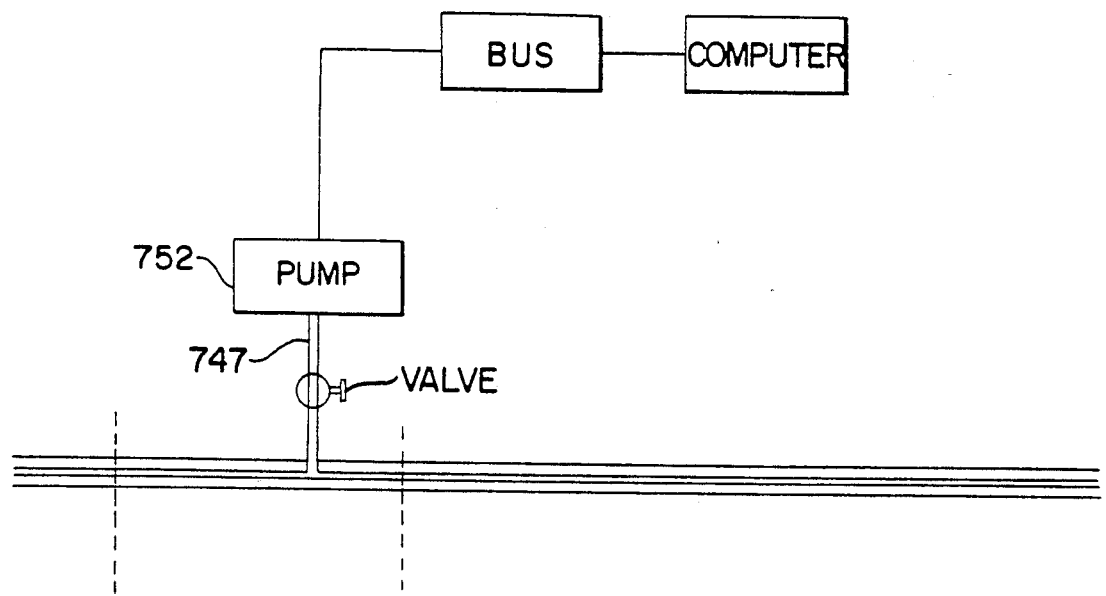
FIG. 30 is a side elevational view of a modified capillary including means for cleaning the capillary.

Another alternative is to recycle the capillary column by a cleaning procedure. As seen in FIG. 30, a T-shaped connection 747 is made near the end of the capillary column with a small tube of material such as metal, glass, plastic, teflon or the like. This connection is now part of the capillary column. The connecting tube is attached to a valve 750 and a vacuum pump 752. This system can be operated through computer control allowing the column to be cleaned in a coordinated manner, i.e., by purging with potassium hydroxide, followed by deionized water and buffer aspirated from cups in the rotatable table 170 or other apparatus and discarded via a teflon port leading to a fluid trap. The capillary column is then ready for a new separation test.

What is claimed is:

1. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past a detector, said first means includes a rotatable table carrying a plurality of sample cups and a holder for holding an end of said capillary tube in operative relation with one of the said cups, said cups containing either buffer solution or a sample to be analyzed, and a T-shaped section of capillary tube inserted in said capillary tube and coupled to a source of cleaning fluid usable to clean said capillary tube.

2. The apparatus defined in claim 1 and including a removable coiled capillary cartridge coupled to said capillary tube.

3. The apparatus defined in claim 1 wherein said capillary tube comprises a plurality of sections coupled together end to end, the internal surfaces of said sections coated with different chemicals.

4. The apparatus defined in claim 3 wherein said chemicals serve to modify the flow of sample material along a capillary tube.

5. The apparatus defined in claim 3 wherein the adjacent ends of said sections are butted together and are secured together by means of surrounding a sleeve which is secured to outer surfaces of said capillary sections.

6. The apparatus defined in claim 1 and including a source of an inert gas coupled to said rotatable table for addition to sample cups therein.

7. The apparatus defined in claim 1 and including a detector coupled to the output end of said capillary tube for detecting the passage of sample therethrough.

8. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past said detector, said first means includes a rotatable table carrying a plurality of sample cups and a holder for holding an end of said capillary tube in operative relation with one of the said cups, said cups containing either buffer solution or a sample to be analyzed, said table including an annular array of holes in which sample cups are seated, said holder being disposed so that said first end of said capillary tube is always positioned over one of said sample cups, said holder including a cylindrical portion which has an aperture which is adapted to receive said first end of said capillary tube and said holder further has a hollow tubular portion which extends downwardly from said cylindrical portion and is adapted to be inserted into a sample cup, said holder having a second aperture to receive an electrode, third means at said second end of said capillary tube including a rotatable table and a plurality of second sample cups carried thereby, a second holder for holding said second end of said capillary tube in operative relation with one of said second sample cups, a first electrode in operative relation with said first end of said capillary tube and a second electrode in operative relation with said second end of said capillary tube, and means for applying electrical potential between said first and second electrodes, said electrical potential being applied with said first and second ends of said capillary tube seated in buffer solution, a vertical post disposed adjacent to said holder and having a slot in its side wall, a vertical rod inside said vertical post and adapted to move vertically up and down, a horizontal arm extending laterally from said vertical rod through said slot, a first electrode on the outer wall of said vertical rod, a lead extending from said first electrode along said horizontal arm into said second aperture in said holder and into said hollow tubular portion, and a second electrode disposed within said vertical post and including a lead coupled to a power supply, said first electrode and said second electrode being positioned so that when said vertical rod moves a predetermined distance, said first and second electrodes make contact with each other.

9. The apparatus defined in claim 8 wherein first electrode is a film electrode.

10. The apparatus defined in claim 8 wherein said capillary tube having an inside diameter in the range of 25 microns to about 200 microns.

11. The apparatus defined in claim 8 and including table drive means for rotating said table with respect to said holder.

12. The apparatus defined in claim 11 and including electronic circuit for automatically synchronizing the operation of said holder drive means and said table drive means so that in a sequence of operations, said holder is raised above said table and then said table is rotated to a position where a selected cup is beneath said holder, and then said holder is lowered so that said first end of said capillary tube is in said cup.

13. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past said detector, said first means includes a rotatable table carrying a plurality of sample cups and a holder for holding an end of said capillary tube in operative relation with one of the said cups, said cups containing either buffer solution or a sample to be analyzed, and said second means includes a second rotatable table carrying a plurality of sample cups and a second holder for holding the other end of said capillary tube, and means for varying the spacing between said first and second holders and the operating length of the capillary tube therebetween.

14. An automated capillary electrophoresis system including a computer for controlling the operation of the system as an electrophoresis system, a bus connected to said a computer, a capillary tube for receiving a sample of a substance to be analyzed and having an input end and an output end, a detector adjacent to said capillary tube for detecting the passage of elements of said sample to be analyzed thereby, a first electorde at said input end of said capillary tube and in operative relation therewith and with fluids contained therein, a second electrode at said output end of said capillary tube and in operative relation therewith and with fluids contained therein, a power supply having terminals adapted to provide a plurality of output voltages, said terminals being coupled to said electrodes for applying voltages therebetween, said power supply also being connected to said bus and to said computer whereby its operation and the application of selected voltages to said electrodes can be controlled and sequenced, a timer control coupled to said bus and to said computer for controlling the time duration of the application of operating voltages to said electrodes by said power supply, a first holder for said input end of said capillary tube, a second holder for said output end of said capillary tube, first holder drive means coupled mechanically to said first holder for driving said first holder and said input end of said capillary tube vertically up and down, said first holder drive means being electrically coupled to said bus and to said computer whereby the operation thereof can be automatically controlled, first holder drive sensor means in operative relation with said first holder drive means for controlling the movement thereof, second holder drive means coupled mechanically to said second holder for driving said second holder and said output end of said capillary tube vertically up and down, said second holder drive being electrically coupled to said bus and to said computer whereby the operation thereof can be automatically controlled, second holder drive sensor means in operative relation with said second holder drive means controlling the up and down movement thereof, a first rotatable table adjacent to said first holder and carrying cups positioned to receive said input end of said capillary tube, a second rotatable adjacent to said second holder and carrying cups positioned to receive said output end of said capillary tube, a first table drive means coupled mechanically to said first rotary table and electronically to said bus and to said computer, first table drive sensor means associated with said first table drive means to control the operation thereof, a second table drive means coupled mechanically to said second rotary table and electrically to said bus and to said computer, second table drive sensor means assoaciated with said second table drive means to control the operation thereof, a clock control means in said computer, said computer operating to:
1. turn on said first and second holder drive means to raise said first and second holders a predetermined amount which raises said first and second holders above said first and second rotary tables respectively, 2. turn on said first and second table drive means to rotate said first and second tables to a starting position under the control of said first and second table drive sensor means, 3. turn on said first and second holder drive means to lower said first and second holders an amount determined by said first and second holder drive sensor means which places said holders and said input end of said capillary tube, which is filled with buffer solution, in a first cup containing a sample substance to be analyzed, 4. cause a sample fluid to be injected into said capillary tube; and 5. cause said sample to flow along said capillary tube.

15. Capillary electrophoresis apparatus comprising a box-like support member having a top wall, front and rear walls and left and right end walls,
  a first box enclosure at one end of said support member,
  a second box enclosure at the opposite end of said support member,
  said box enclosures each including a base member, left and right sidewalls, front and rear walls and a removable cover,
  a first rotatable table disposed within said first box enclosure and rotatably supported on the base member thereof,
  a plurality of apertures in said first table and a sample cup seated in each of said apertures,
  a vertically moveable first post disposed adjacent to said first table and including a first hollow tube extending downwardly therefrom over said apertures in said first table, said first hollow being adapted to be moved into and out of a sample cup when said first arm moves down and up,
  a first electrode extending into said first hollow tube,
  a second rotatable table disposed within said second box enclosure and rotatably supported on the base member thereof,
  a plurality of apertures in said second table and a sample cup seated in each of said apertures,
  a vertically moveable second post disposed adjacent to said second table and including a second hollow tube extending downwardly therefrom over said apertures in said second table,
  said hollow tube being adapted to be moved into and out of a sample cup when said second arm moves down and up,
  a second electrode extending into said second hollow tube,
  said first and second electrodes being adapted to have electrical power coupled thereto,
  a capillary tube extending from said first box enclosure to said second box enclosure and having one end disposed within said first tube and the other end of said capillary tube disposed within said second hollow tube,
  a detector disposed adjacent to said capillary tube for detecting the passage of charged particles therethrough, and
  a pump coupled to the output end of said capillary tube, said pump comprising a miniature pump mounted inside said housing.

16. The apparatus defined in claim 15 wherein said rotatable table is supported on a vertical post which extends below the top wall of said support member and includes a lower post portion thereat,
  a motor coupled to said lower post portion beneath said top wall of said support member,
  a horizontal sensor disk secured to said lower post portion and adapted to be rotated thereby, and
  an optical sensor coupled to said horizontal disk and adapted to operate said motor in response to the position of said sensor disk with respect to said sensor.

17. The apparatus defined in claim 16 wherein said motor is supported on the lower surface of said top wall of said support member.

18. The apparatus defined in claim 15 and including power interlock means associated with the covers of said boxes for disconnecting electrical power when a cover is removed.

19. The apparatus defined in claim 15 and including a first hollow, tubular vertical post having a slot in its wall with said vertically moveable first post disposed therewithin,
  a first horizontal arm extending from said vertically moveable first post through said slot and carrying said first hollow tube at its outer end
  said vertically moveable first post having a lower post portion extending downwardly through the base member of said first box to beneath said top wall of said support member,
  a first motor coupled to said lower post position to drive it up and down,
  a first optical sensor positioned adjacent to said lower post position,
  a first means carried on said lower post position and positioned to operate with said first optical sensor to contorl the operation of said first motor,
  a second hollow tubular vertical post having a slot in its wall with said vertically moveable second post disposed therewithin,
  a second horizontal arm extending from said vertically moveable second post carrying said second hollow tube at its outer end, said vertically moveable second post having a lower portion extending downwardly through the base member of said second box to beneath said top wall of said support member,
  a second motor coupled to said lower post portion of said vertically moveable second arm to drive it up and down,
  a second optical sensor positioned adjacent to said lower post portion of said vertically moveable second arm, and
  a second means carried on said lower post portion of said vertically moveable second arm and positioned to operate with said second optical sensor to control the operation of said second motor.

20. Capillary electrophoresis apparatus comprising a box-like support member having a top wall, front and rear walls and left and right end walls,
  said top wall having a top surface and a bottom surface,
  a first box enclosure at one end of said support member,
  a second box enclosure at the opposite end of said support member,
  said box enclosures each including a base member, left and right sidewalls, front and rear walls and a removable cover,
  an aperture in said top wall of said box-like support member, said aperture extending along a portion of the length at said top wall, a first rotatable table disposed within said first box enclosure and rotatably supported on the base member thereof, a plurality of apertures in said first table and a sample cup seated in each of said apertures, a second rotatable table disposed within said second box enclosure and rotatably supported on the base member thereof, a plurality of apertures in said second table and a sample cup seated in each of said apertures, a capillary tube extending from said first box enclosure to said second box enclosure and having one end disposed in operative relation with said first table and the other end of said capillary tube disposed in operative relation with said second table, and a detector disposed adjacent to said capillary tube for detecting the passage of charged particles therethrough, said first box being mounted on said top wall, said second box being slidably mounted on said top wall and secured to mounting means disposed beneath said top wall and within said box-like support member.

21. The apparatus defined in claim 20 wherein said last-named means includes a first rotatable wheel and a second rotatable wheel spaced from said first rotatable wheel, a drive belt coupled to said rotatable wheels, a drive motor coupled to said first rotatable wheel, and means coupled to said belt and said second box whereby operation of said drive motor and movement of said drive belt cause said second box to slide along said top wall to assure different spacings from said first box.

22. The apparatus defined in claim 21 and including a bellowtype screen disposed along said aperture in said top wall to prevent foreign objects from falling into said box-like support member.

23. Capillary electrophoresis apparatus comprising a box-like support member having a top wall, front and rear walls, and left and right end walls, said top wall having a top surface and a bottom surface, a first box enclosure at one end of said top wall of said support member, a second box enclosure at the opposite end of said top wall of said support member, means supporting a capillary tube between said first box and said second box, and means associated with said box-like support member for varying the spacing between said first box and said second box whereby capillary tubes of different lengths can be supported therebetween.

24. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past said detector, said first means includes a rotatable table carrying a plurality of sample cups and a holder for holding an end of said capillary tube in operative relation with one of the said cups, said cups containing either buffer solutions or a sample to be analyzed, a magnifying glass coupled to said capillary tube for viewing the flow of fluid through said capillary tube, and a pump coupled to the output end of said capillary tube.

25. The apparatus defined in claim 24 wherein said magnifying glass permits observation of the sample meniscus in said capillary tube to determine electroosmotic flow therein.

26. The apparatus defined in claim 24 wherein said magnifying glass permits observation of the sample meniscus in said capillary tube to determine osmotic flow therein.

27. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past said detector, said first means includes a rotatable table carrying a plurality of sample cups and a holder for holding an end of said capillary tube in operative relation with one of the said cups, said cups containing either buffer solution or a sample to be analyzed, and a source of an oxygen absorbent gas coupled to said rotatable table for introduction of said gas into sample cups to remove air bubbles therefrom.

28. The apparatus defined in claim 27 wherein said gas is a gas selected from the group of gases including helium, nitrogen and argon.

29. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past said detector, said first means includes a rotatable table carrying a plurality of sample cups and a holder for holding an end of said capillary tube in operative relation with one of the said cups, said cups containing either buffer solution or a sample to be analyzed, and including means for operating said second means to cause said electrical potential to be cyclically reversed to cause said sample to move first in one direction and then in the opposite direction past said detector to provide a series of detector pulses for identification of the sample.

30. The method of detecting the nature of a sample of a substance by capillary electrophoresis comprising the steps of passing a substance to be analyzed in one direction through a detector to obtain a pulse representative of the optical wavelength of said sample, passing said substance in the opposite direction through said detector to obtain a second pulse representat0ve of the optical wavelength of said sample and, continuing the process of passing said substance back and forth through said detector to obtain a series of pulses which combine to provide accurate identification of the sample.

31. Apparatus for analyzing a sample material comprising a capillary tube a detector adjacent to said capillary tube and adapted to provide an output detector pulse when a sample material passes along said capillary tube and through said detector, a source of sample material at one end of said capillary tube to be passed down said tube to said detector, electrical means connected across said capillary tube for causing said sample material to pass in a first direction along said capillary tube through said detector to provide a first detection pulse, said electrical means being reversible to cause said sample material to flow in the reverse direction to said first direction to cause said sample material to pass through said detector to provide a second detector pulse, and means for toggling said electrical means to cause said sample substance to pass back and forth through said detector and providing thereby multiple detector pulses.

32. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past a detector, said first means includes a rotatable table carrying a plurality of sample cups and a holder for holding an end of said capillary tube in operative relation with one of the said cups, said cups containing either buffer solution or a sample to be analyzed, and said capillary tube is in the form of a coil of glass tubing.

33. Capillary electrophoresis apparatus including a capillary tube having an inlet end and an outlet end for receiving a sample to be identified and for passing the sample along the length of the capillary, a porous glass tube receiving the outlet end of said capillary tube and an auxiliary tube in said porous glass tube having one end adjacent to the outlet end of said capillary tube and adapted to receive a sample from said capillary tube, said auxiliary tube having an outlet end from which the sample exits to a collection means.

34. The apparatus defined in claim 33 wherein the outlet end of said auxiliary tube is positioned over a rotatable table, for receiving samples from said auxiliary tube.

35. The apparatus defined in claim 34 and including a sensor at the outlet end of said auxiliary tube, an optical glass fiber coupled at one end to said sensor and at the other end to a detector for detecting the passage of a sample through said auxiliary tube whereby rotation of said rotatable table may be effected as each sample appear.

36. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past a detector, said first means including a rotatable table carrying a plurality of sample cups and a holder for holding anend of said capillary tube in operativerelation with one of said cups, said cups containing either buffer solution or a sample to be analyzed, and a plurality of chemical substances spaced apart along the length of said capillary tube, each of said chemical substances having a specific action with respect to constituent molecules contained within a sample flowing along said capillary and either attracting a molucule for later elution or permitting a molecule to pass along the capillary tube.

37. Capillary electrophoresis apparatus comprising a capillary tube of the type which can be electrically charged, said capillary tube having first and second ends, first means at said first end of said capillary tube providing a source of buffer solution and a source of a sample substance to be analyzed, second means coupled to said apparatus for applying electrical potential across said capillary tube whereby a sample flows through said capillary tube and past a detector, and a plurality of chemical substances spaced apart along the length of said capillary tube, each of said chemical substances having a specific action with respect to constituent molecules contained within a sample flowing along said capillary and either attracting a molucule for later elution or permitting a molecule to pass along the capillary tube.

38. The apparatus defined in claim 37 wherein said chemical substances are in the form of coatings on the wall of said capillary tube.

39. The apparatus defined in claim 37 wherein said chemical substances are in bulk form and disposed within said capillary tube.

40. The apparatus defined in claim 39 wherein said chemical substances are coated on globules of insulating material.

* * * * *